United States Patent
Bingel et al.

(10) Patent No.: US 7,053,160 B1
(45) Date of Patent: May 30, 2006

(54) METALLOCENE MONOHALOGENIDES

(75) Inventors: Carsten Bingel, Kriftel (DE); Hans-Herbert Brintzinger, Tägerwilen (DE); Hans-Robert-Hellmuth Damrau, Constance (DE); Patrik Müller, Kaiserslautern (DE); Jürgen Suhm, Ludwigshafen (DE)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 09/701,658

(22) PCT Filed: Nov. 18, 1999

(86) PCT No.: PCT/EP99/08851

§ 371 (c)(1),
(2), (4) Date: Nov. 30, 2000

(87) PCT Pub. No.: WO00/31090

PCT Pub. Date: Jun. 2, 2000

(30) Foreign Application Priority Data

Nov. 25, 1998 (DE) ................................ 198 54 350

(51) Int. Cl.
  C08F 4/76 (2006.01)
  C08F 4/52 (2006.01)
  C07F 17/00 (2006.01)

(52) U.S. Cl. .................. 526/170; 526/160; 526/941; 526/943; 526/130; 556/53

(58) Field of Classification Search ................ 526/126, 526/943, 160, 161, 170; 502/103; 556/11, 556/53, 56, 13, 52

See application file for complete search history.

(56) References Cited

U.S. PATENT DOCUMENTS

| | | | |
|---|---|---|---|
| 4,752,597 A | 6/1988 | Turner | 502/104 |
| 5,017,714 A | 5/1991 | Welborn | 556/12 |
| 5,103,030 A | 4/1992 | Rohrmann | 556/12 |
| 5,145,819 A | 9/1992 | Winter | 502/117 |
| 5,171,799 A * | 12/1992 | Kioka et al. | 526/127 |
| 5,304,614 A | 4/1994 | Winter | 526/127 |
| 5,455,366 A | 10/1995 | Rohrmann | 556/8 |
| 5,543,373 A * | 8/1996 | Winter et al. | 502/103 |
| 5,543,535 A | 8/1996 | Lisowsky | 556/11 |
| 5,700,750 A | 12/1997 | Tsutsui et al. | 502/117 |
| 5,770,753 A | 6/1998 | Küber | 556/11 |
| 5,795,838 A * | 8/1998 | Tsutsui et al. | 502/103 |
| 5,798,427 A * | 8/1998 | Foster et al. | 526/352 |
| 5,807,801 A | 9/1998 | Tsutsui et al. | 502/119 |

FOREIGN PATENT DOCUMENTS

| | | |
|---|---|---|
| EP | 120 368 | 12/1984 |
| EP | 287 666 | 10/1988 |
| EP | 320 762 | 6/1989 |
| EP | 384171 A1 | 8/1990 |
| EP | 416 815 | 3/1991 |
| EP | 0 629 632 | 12/1991 |
| EP | 485 823 | 5/1992 |
| EP | 537 686 | 4/1993 |
| EP | 549 900 | 7/1993 |
| EP | 576 970 | 1/1994 |
| EP | 629632 A2 * | 12/1994 |
| EP | 669 340 | 8/1995 |
| EP | 1 028 123 | 8/2000 |
| JP | H3-74415 | 3/1991 |
| WO | 87/03887 | 7/1987 |
| WO | 98/40331 | 9/1998 |
| WO | WO 98/56831 A1 * | 12/1998 |

OTHER PUBLICATIONS

Schmidt, K.; Reinmuth, A.; Rief, U.; Diebold, J.; Brintzinger, H. H. Organometallics 1997, 16, 1724.*
Dormand, A.; Tirouflet, J.; Le Moigne, F. J. Organomet. Chem. 1975, 101, 71.*
Repo. T.; Jany, G.; Salo, M.; Polamo, M.; Leskela, M. J. Organomet. Chem. 1997, 541, 363.*
Wochner, F.; Brintzinger, H. H. J. Organomet. Chem. 1986, 309, 66.*
Barriola, A. M.; Cano, A. M.; Cuenca, T.; Fernandez, F. J.; Gomez-Sal, P.; Manzanero, A.; Royo, P. J. Organomet. Chem. 1997, 542, 247.*
Repo et al. J. Organomet. Chem. 1997, 541, 363-366.*
Angew.Chem.1995,197,1255-1283, Brintzinger.
J.Organomet.Chem. 323(1982)233-247, Wild et al.
Chem.Abst, XP-002128403.
J.Organomet.Chem.101(1975)71-94, Dormond et al.
J.Organomet.Chem. 541(1997)363-366, Repo et al.
Chem.Abst. XP 002128401.
Chem.Abst. XP 002128402.
Chem.Abst. XP 002128399.
J. Organomet.Chem., 165(1979)319-327;Dormond et al.
J.Organomet.125(1977)63-69;Dormond et al.
Chem.Abst. XP 002128400.

* cited by examiner

*Primary Examiner*—David W. Wu
*Assistant Examiner*—Rip A. Lee
(74) *Attorney, Agent, or Firm*—Novak Druce Deluca & Quigg, LLP; Jason D. Voight

(57) ABSTRACT

Novel metallocene monohalides can be used in the polymerization of olefins.

18 Claims, No Drawings

METALLOCENE MONOHALOGENIDES

The present invention relates to specifically substituted metallocenes, a process for preparing them and their use in the polymerization of olefins.

Metallocenes can, if desired in combination with one or more cocatalysts, be used as catalyst components for the polymerization and copolymerization of olefins. In particular, halogen-containing metallocenes are used as catalyst precursors which can be converted into a polymerization-active cationic metallocene complex by means of, for example, an aluminoxane (EP-A-129368).

The preparation of metallocenes is known per se (U.S. Pat. No. 4,752,597; U.S. Pat. No. 5,017,714; EP-A-320762; EP-A-416815; EP-A-537686; EP-A-669340; H. H. Brintzinger et al.; Angew. Chem., 107 (1995), 1255; H. H. Brintzinger et al., J. Organomet. Chem. 232 (1982), 233). This can be achieved, for example, by reacting cyclopentadienyl-metal compounds with halides of transition metals such as titanium, zirconium and hafnium. The metallocene dihalides formed, generally the metallocene dichlorides, are, in the case of the industrially interesting racemic ansa-bisindenyl-metallocenes required for the preparation of isotactic polypropylene (EP 0485823, EP 0549900, EP 0576970, WO 98/40331), generally sparingly soluble compounds.

Both in the preparation of polymerization-active cationic metallocene catalyst systems in unsupported or supported form and also for the purification of the racemic metallocene, i.e. the catalyst precursor, by crystallization techniques, better solubility of the industrially interesting metallocenes would be desirable.

It is an object of the present invention to find readily soluble metallocenes which after conversion into the polymerization-active species display at least the same polymerization performance as the catalyst systems prepared from sparingly soluble metallocene dichlorides.

We have found that this object is achieved by specifically substituted metallocenes, namely metallocene monohalides.

The present invention provides compounds of the formula (I),

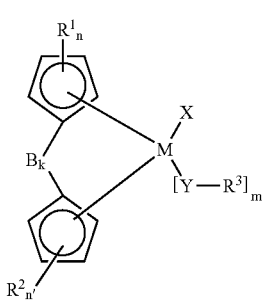

(I)

where

M is a metal of transition group III, IV, V or VI of the Periodic Table of the Elements, in particular Ti, Zr or Hf, particularly preferably zirconium, $R^1$ are identical or different and are each $Si(R^{12})_3$, where $R^{12}$ are identical or different and are each a hydrogen atom or a $C_1$–$C_{40}$-group, preferably $C_1$–$C_{20}$-alkyl, $C_1$–$C_{10}$-fluoroalkyl, $C_1$–$C_{10}$-alkoxy, $C_6$–$C_{20}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or $R^1$ is a $C_1$–$C_{30}$-group, preferably $C_1$–$C_{25}$-alkyl such as methyl, ethyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy, or two or more radicals $R^1$ may be connected to one another in such a way that the radicals $R^1$ and the atoms of the cyclopentadienyl ring which connect them form a $C_4$–$C_{24}$-ring system which may in turn be substituted, $R^2$ are identical or different and are each $Si(R^{12})_3$, where $R^{12}$ are identical or different and are each a hydrogen atom or a $C_1$–$C_{40}$-group, preferably $C_1$–$C_{20}$-alkyl, $C_1$–$C_{10}$-fluoroalkyl, $C_1$–$C_{10}$-alkoxy, $C_6$–$C_{14}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or $R^2$ is a $C_1$–$C_{30}$-group, preferably $C_1$–$C_{25}$-alkyl such as methyl, ethyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy, or two or more radicals $R^2$ may be connected to one another in such a way that the radicals $R^2$ and the atoms of the cyclopentadienyl ring which connect them form a $C_4$–$C_{24}$-ring system which may in turn be substituted, $R^3$ are identical or different and are each a $C_1$–$C_{40}$-group, preferably $C_1$–$C_{25}$-alkyl such as methyl, ethyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl such as pyridyl, furyl or quinolyl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $c_7$–$C_{30}$-arylalkyl or fluorinated $C_7$–$C_{30}$-alkylaryl, X is a halogen atom, in particular chlorine, Y is an element of main group VI of the Periodic Table of the Elements or a fragment $CH_2$, $CR^3_2$, $NR^3$, $PR^3$ or $P(=O)R^3$, in particular oxygen, sulfur or $NR^3$, particularly preferably oxygen, n is from 1 to 5 when k=0, and n is from 0 to 4 when k=1, n' is from 1 to 5 when k=0, and n' is from 0 to 4 when k=1, m is from 1 to 3, preferably 1, k is zero or 1, with k=0 giving an unbridged metallocene and k=1 giving a bridged metallocene, preference being given to k=1, and B is a bridging structural element between the two cyclopentadienyl rings.

Examples of B are $M^3R^{13}R^{14}$ groups, where $M^3$ is carbon, silicon, germanium or tin and $R^{13}$ and $R^{14}$ are identical or different and are each a $C_1$–$C_{20}$-hydrocarbon-containing group such as $C_1$–$C_{10}$-alkyl, $C_6$–$C_{14}$-aryl or trimethylsilyl. B is preferably $CH_2$, $CH_2CH_2$, $CH(CH_3)CH_2$, $CH(C_4Hg)C(CH_3)_2$, $C(CH_3)_2$, $(CH_3)_2Si$, $(CH_3)_2Ge$, $(CH_3)_2Sn$, $(C_6H_5)_2Si$, $(C_6H_5)(CH_3)Si$, $Si(CH_3)(SiR^{20}R^{21}R^{22})$, $(C_6H_5)_2Ge$, $(C_6H_5)_2Sn$, $(CH_2)_4S_1$, $CH_2Si(CH_3)_2$, $o$-$C_6H_4$ or $2,2'$-$(C_6H_4)_2$, where $R^{20}$, $R^{21}$ and $R^{22}$ are identical or different and are each a $C_1$–$C_{20}$-hydrocarbon-containing group such as $C_1$–$C_{10}$-alkyl or $C_6$–$C_{14}$-aryl. It is also possible for B together with one or more radicals $R^1$ and/or $R^2$ to form a monocyclic or polycyclic ring system. Preference is given to bridged metallocene compounds of the formula (I), in particular those in which k is equal to 1 and one or both cyclopentadienyl rings are substituted in such a way that they form an indenyl ring. The indenyl ring is preferably substituted, in particular in the 2 position, 4 position, 2,4,5 positions, 2,4,6 positions, 2,4,7 positions or 2,4,5,6 positions, by $C_1$–$C_{20}$-groups such as $C_1$–$C_{18}$-alkyl or $C_6$–$C_{18}$-aryl, where two or more substituents of the indenyl ring may together also form a ring system.

Particular preference is given to bridged metallocene compounds of the formula (II),

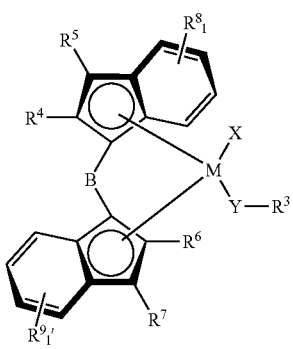

(II)

where

M is Ti, Zr or Hf, particularly preferably zirconium, $R^3$ are identical or different and are each a $C_1$–$C_{30}$-group, preferably $C_3$–$C_{10}$-alkyl such as isopropyl, tert-butyl, cyclohexyl or octyl, $C_6$–$C_{24}$-aryl, $C_5$–$C_{24}$-heteroaryl such as pyridyl, furyl or quinolyl, $C_7$–$C_{30}$-arylalkyl, $C_7$–$C_{30}$-alkylaryl, fluorinated $C_6$–$C_{24}$-aryl, fluorinated $C_7$–$C_{30}$-arylalkyl or fluorinated $C_7$–$C_{30}$-alkylaryl, $R^4$, $R^6$ are identical or different and are each a hydrogen atom, a $C_1$–$C_{20}$-group, preferably $C_1$–$C_{18}$-alkyl such as methyl, ethyl, n-butyl, cyclohexyl or octyl, $C_2$–$C_{10}$-alkenyl, $C_3$–$C_{15}$-alkylalkenyl, $C_6$–$C_{18}$-aryl, $C_5$–$C_{18}$-heteroaryl such as pyridyl, furyl or quinolyl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, $R^5$, $R^7$ are identical or different and are each a hydrogen atom, a $C_1$–$C_{20}$-group, preferably $C_1$–$C_{18}$-alkyl such as methyl, ethyl, n-butyl, cyclohexyl or octyl, $C_2$–$C_{10}$-alkenyl, $C_3$–$C_{15}$-alkylalkenyl, $C_6$–$C_{18}$-aryl, $C_5$–$C_{18}$-heteroaryl such as pyridyl, furyl or quinolyl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, $R^8$ and $R^9$ are identical or different and are each a hydrogen atom, a halogen atom or a $C_1$–$C_{20}$-group, preferably a linear or branched $C_1$–$C_{18}$-alkyl group such as methyl, ethyl, tert-butyl, cyclohexyl or octyl, $C_2$–$C_{10}$-alkenyl, $C_3$–$C_{15}$-alkylalkenyl, a $C_6$–$C_{18}$-aryl group which may be substituted, in particular phenyl, tolyl, xylyl, tert-butylphenyl, ethylphenyl, di-tert-butylphenyl, naphthyl, acenaphthyl, phenanthrenyl or anthracenyl, $C_5$–$C_{18}$-heteroaryl such as pyridyl, furyl or quinolyl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, or two radicals $R^8$ or $R^9$ may form a monocyclic or polycyclic ring system which may in turn be substituted, X is a halogen atom, in particular chlorine, Y is an element of main group VI of the Periodic Table of the Elements or a fragment $CH_2$, $CR^3_2$, $NR^3$, $PR^3$ or $P(=O)R^3$, in particular oxygen, sulfur or $NR^3$, particularly preferably oxygen, l, l' are identical or different and are each an integer from zero to 4, preferably 1 or 2, particularly preferably 1, B is a bridging structural element between the two indenyl radicals.

Examples of B are $M^3R^{13}R^{14}$ groups, where $M^3$ is carbon, silicon, germanium or tin, preferably carbon or silicon, and $R^{13}$ and $R^{14}$ are identical or different and are each hydrogen or a $C_1$–$C_{20}$-hydrocarbon-containing group such as $C_1$–$C_{10}$-alkyl, $C_6$–$C_{14}$-aryl or trimethylsilyl. B is preferably $CH_2$, $CH_2CH_2$, $CH(CH_3)CH_2$, $CH(C_4H_9)C(CH_3)_2$, $C(CH_3)_2$, $(CH_3)_2Si$, $(CH_3)_2Ge$, $(CH_3)_2Sn$, $(C_6H_5)_2C$, $(C_6H_5)_2Si$, $(C_6H_5)(CH_3)Si$, $Si(CH_3)(SiR^2OR^{21}R^{22})$, $(C_6H_5)_2Ge$, $(C_6H_5)_2Sn$, $(CH_2)_4S_1$, $CH_2Si(CH_3)_2$, o-$C_6H_4$ oder 2,2'-$(C_6H_4)_2$, where $R^{20}$, $R^{21}$ and $R^{22}$ are identical or different and are each a $C_1$–$C_{20}$-hydrocarbon-containing group such as $C_1$–$C_{10}$-alkyl or $C_6$–$C_{14}$-aryl.

Very particular preference is given to bridged metallocene compounds of the formula (II), in which M is zirconium, $R^3$ is a $C_1$–$C_{30}$-group, preferably $C_3$–$C_{10}$-alkyl such as isopropyl, tert-butyl, cyclohexyl or octyl, $C_6$–$C_{24}$-aryl, $C_5$–$C_{24}$-heteroaryl such as pyridyl, furyl or quinolyl, $C_7$–$C_{30}$-arylalkyl, $C_7$–$C_{30}$-alkylaryl, fluorinated $C_6$–$C_{24}$-aryl, fluorinated $C_7$–$C_{30}$-arylalkyl or fluorinated $C_7$–$C_{30}$-alkylaryl, $R^4$, $R^6$ are identical or different and are each a hydrogen atom or a $C_1$–$C_{12}$-alkyl group, preferably an alkyl group such as methyl, ethyl, n-propyl, isopropyl, n-butyl, n-pentyl, n-hexyl or octyl, particularly preferably methyl or ethyl, $R^5$, $R^7$ are hydrogen atoms, $R^8$ and $R^9$ are identical or different and are each a hydrogen atom, a halogen atom or a $C_1$–$C_{20}$-group, preferably a linear or branched $C_1$–$C_8$-alkyl group such as methyl, ethyl, tert-butyl, cyclohexyl or octyl, $C_2$–$C_6$-alkenyl, $C_3$–$C_6$-alkylalkenyl, a $C_6$–$C_{18}$-aryl group which may be substituted, in particular phenyl, tolyl, xylyl, tert-butylphenyl, ethylphenyl, di-tert-butylphenyl, naphthyl, acenaphthyl, phenanthrenyl or anthracenyl, $C_5$–$C_{16}$-heteroaryl such as pyridyl, furyl or quinolyl, $C_7$–$C_{12}$-arylalkyl, $C_7$–$C_{12}$-alkylaryl, fluorinated $C_1$–$C_8$-alkyl, fluorinated $C_6$–$C_{18}$-aryl, fluorinated $C_7$–$C_{12}$-arylalkyl or fluorinated $C_7$–$C_{12}$-alkylaryl, X is chlorine Y is oxygen, l, l' are identical or different and are each an integer from zero to 4, preferably 1 or 2, particularly preferably 1, B is a bridging structural element between the two indenyl radicals, where B is preferably $(CH_3)_2Si$, $(CH_3)_2Ge$, $(C_6H_5)_2Si$, $(C_6H_5)(CH_3)S_1$, $CH_2CH_2$, $CH(CH_3)CH_2$, $CH(C_4H_9)C(CH_3)_2$, $CH_2$, $C(CH_3)_2$, $(C_6H_5)_2C$, particularly preferably $(CH_3)_2S_1$, $CH_2$ or $CH_2CH_2$.

The novel metallocenes of the formulae I and II have a significantly better solubility in inert organic solvents than do the corresponding metallocene dichlorides (X=Cl and Y—$R^3$=Cl). A significantly better solubility is intended to mean that the molar concentrations in organic solvents are at least doubled, preferably more than quadrupled and very particularly preferably increased by a factor of more than eight. A further advantage is that the compounds of the present invention display a better crystallization behavior from inert organic solvents, which aids their purification.

As inert organic solvents for metallocenes, it is customary to use aliphatic or aromatic hydrocarbons, and also halogen-containing, oxygen-containing or nitrogen-containing hydrocarbons. Without seeking to be exhaustive, examples of the individual solvent classes are heptane, toluene, dichlorobenzene, methylene chloride, tetrahydrofuran and triethylamine.

In place of the pure chiral bridged metallocene compounds of the formula (II) (pseudo-rac), it is also possible to use mixtures of the metallocenes of the formula (II) and the corresponding pseudo-meso metallocenes of the formula (IIa) for preparing catalysts.

(II)

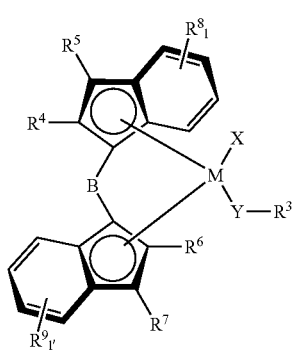

pseudo-rac (IIa)

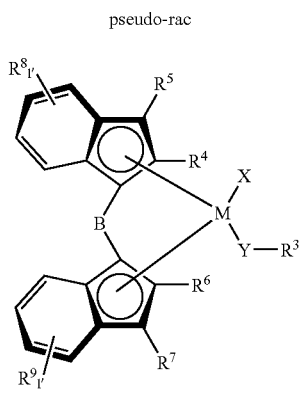

pseudo-meso

Illustrative but nonlimiting examples of metallocenes according to the present invention are:
dimethylsilanediylbis(indenyl)zirconium monochloride mono(2,4-di-tert-butylphenoxide)
dimethylsilanediylbis(2-methylindenyl)zirconium monochloride mono(2,4-di-tert-butylphenoxide)
methylidenebis(2-methylindenyl)zirconium monochloride mono(2,4-di-tert-butylphenoxide)
isopropylidenebis(2-methylindenyl)zirconium monochloride mono(2,4-di-tert-butylphenoxide)
dimethylsilanediylbis(2-methylbenzoindenyl)zirconium monochloride mono(2,4-di-tert-butylphenoxide)
dimethylsilanediylbis(4-naphthylindenyl)zirconium monochloride mono(2,4-di-tert-butylphenoxide)
dimethylsilanediylbis(2-methyl-4-(1-naphthyl)indenyl)zirconium monochloride mono(2,4-di-tert-butylphenoxide)
methylidenebis(2-methyl-4-(1-naphthyl)indenyl)zirconium monochloride mono(2,4-di-tert-butylphenoxide)
isopropylidenebis(2-methyl-4-(1-naphthyl)indenyl)zirconium monochloride mono(2,4-di-tert-butylphenoxide)
dimethylsilanediylbis(2-methyl-4-(2-naphthyl)indenyl)zirconium monochloride mono(2,4-di-tert-butylphenoxide)
dimethylsilanediylbis(2-methyl-4-phenylindenyl)zirconium monochloride mono(2,4-di-tert-butylphenoxide)
methylidenebis(2-methyl-4-phenylindenyl)zirconium monochloride mono(2,4-di-tert-butylphenoxide)
Isopropylidenebis(2-methyl-4-phenylindenyl)zirconium monochloride mono(2,4-di-tert-butylphenoxide)
dimethylsilanediylbis(2-methyl-4-t-butylindenyl)zirconium monochloride mono(2,4-di-tert-butylphenoxide)
dimethylsilanediylbis(2-methyl-4-isopropylindenyl)zirconium monochloride mono(2,4-di-tert-butylphenoxide)
dimethylsilanediylbis(2-methyl-4-ethylindenyl)zirconium monochloride mono(2,4-di-tert-butylphenoxide)
dimethylsilanediylbis(2,4-dimethylindenyl)zirconium monochloride mono(2,4-di-tert-butylphenoxide)
dimethylsilanediylbis(2-ethylindenyl)zirconium monochloride mono(2,4-di-tert-butylphenoxide)
dimethylsilanediylbis(2-ethyl-4-ethylindenyl)zirconium monochloride mono(2,4-di-tert-butylphenoxide)
dimethylsilanediylbis(2-ethyl-4-phenylindenyl)zirconium monochloride mono(2,4-di-tert-butylphenoxide)
dimethylsilanediylbis(2-methyl-4,5-benzoindenyl)zirconium monochloride mono(2,4-di-tert-butylphenoxide)
methylidenebis(2-methyl-4,5-benzoindenyl)zirconium monochloride mono(2,4-di-tert-butylphenoxide)
isopropylidenebis(2-methyl-4,5-benzoindenyl)zirconium monochloride mono(2,4-di-tert-butylphenoxide)
dimethylsilanediylbis(2-methyl-4,6-diisopropylindenyl)zirconium monochloride mono(2,4-di-tert-butylphenoxide)
dimethylsilanediylbis(2-methyl-4,5-diisopropylindenyl)zirconium monochloride mono(2,4-di-tert-butylphenoxide)
dimethylsilanediylbis(2,4,6-trimethylindenyl)zirconium monochloride mono(2,4-di-tert-butylphenoxide)
dimethylsilanediylbis(2,5,6-trimethylindenyl)zirconium monochloride mono(2,4-di-tert-butylphenoxide)
dimethylsilanediylbis(2,4,7-trimethylindenyl)zirconium monochloride mono(2,4-di-tert-butylphenoxide)
dimethylsilanediylbis(2-methyl-5-isobutylindenyl)zirconium monochloride mono(2,4-di-tert-butylphenoxide)
dimethylsilanediylbis(2-methyl-5-t-butylindenyl)zirconium monochloride mono(2,4-di-tert-butylphenoxide)
methyl(phenyl)silanediylbis(2-methyl-4-phenylindenyl)zirconium monochloride mono(2,4-di-tert-butylphenoxide)
methyl(phenyl)silanediylbis(2-methyl-4,6-diisopropylindenyl)zirconium monochloride mono(2,4-di-tert-butylphenoxide)
methyl(phenyl)silanediylbis(2-methyl-4-isopropylindenyl)zirconium monochloride mono(2,4-di-tert-butylphenoxide)
methyl(phenyl)silanediylbis (2-methyl-4,5-benzoindenyl)zirconium monochloride mono(2,4-di-tert-butylphenoxide)
methyl(phenyl)silanediylbis(2-methyl-4,5-(methylbenzo)indenyl)zirconium monochloride mono(2,4-di-tert-butylphenoxide)
methyl(phenyl)silanediylbis(2-methyl-4,5-(tetramethylbenzo)indenyl)zirconium monochloride mono(2,4-di-tert-butylphenoxide)
methyl(phenyl)silanediylbis(2-methylindenyl)zirconium monochloride mono(2,4-di-tert-butylphenoxide)
methyl(phenyl)silanediylbis(2-methyl-5-isobutylindenyl)zirconium monochloride mono(2,4-di-tert-butylphenoxide)
1,2-ethanediylbis(2-methyl-4-phenylindenyl)zirconium monochloride mono(2,4-di-tert-butylphenoxide)
1,4-butanediylbis(2-methyl-4-phenylindenyl)zirconium monochloride mono(2,4-di-tert-butylphenoxide)
1,2-ethanediylbis(2-methyl-4,6-diisopropylindenyl)zirconium monochloride mono(2,4-di-tert-butylphenoxide)

1,4-butanediylbis(2-methyl-4-isopropylindenyl)zirconium monochloride mono(2,4-di-tert-butylphenoxide)
1,4-butanediylbis(2-methyl-4,5-benzoindenyl)zirconium monochloride mono(2,4-di-tert-butylphenoxide)
1,2-ethanediylbis(2-methyl-4,5-benzoindenyl)zirconium monochloride mono(2,4-di-tert-butylphenoxide)
1,2-ethanediylbis(2,4,7-trimethylindenyl)zirconium monochloride mono(2,4-di-tert-butylphenoxide)
1,2-ethanediylbis(2-methylindenyl)zirconium monochloride mono(2,4-di-tert-butylphenoxide)
1,4-butanediylbis(2-methylindenyl)zirconium monochloride mono(2,4-di-tert-butylphenoxide)
[4-($\eta^5$-cyclopentadienyl)-4,6,6-trimethyl($\eta^5$-4,5-tetrahydropentalene)]zirconium monochloride mono(2,4-di-tert-butylphenoxide)
[4-($\eta^5$-3'-trimethylsilylcyclopentadienyl)-4,6,6-trimethyl ($\eta^5$-4,5-tetrahydropentalene)]zirconium monochloride mono(2,4-di-tert-butylphenoxide)
[4-($\eta^5$-3'-isopropylcyclopentadienyl)-4,6,6-trimethyl($^5$-4,5-tetrahydropentalene)]zirconium monochloride mono(2,4-di-tert-butylphenoxide)
[4-($\eta^5$-cyclopentadienyl)-4,7,7-trimethyl($\eta^5$-4,5,6,7-tetrahydro-indenyl)]zirconium monochloride mono(2,4-di-tert-butylphenoxide)
[4-($\eta^5$-3'-tert-butylcyclopentadienyl)-4,7,7-trimethyl-($\eta^5$-4,5,6,7-tetrahydroindenyl)]zirconium monochloride mono (2,4-di-tert-butylphenoxide)
4-($\eta^5$-3'-methylcyclopentadienyl)-4,7,7-trimethyl($^5$-4,5,6,7-tetrahydroindenyl)]zirconium monochloride mono(2,4-di-tert-butylphenoxide)
4-($\eta^5$-3'-trimethylsilylcyclopentadienyl)-2-trimethylsilyl-4,7,7-trimethyl($\eta^5$-4,5,6,7-tetrahydroindenyl)]zirconium monochloride mono(2,4-di-tert-butylphenoxide)
bis(1,3-dimethylcyclopentadienyl)zirconium monochloride mono(2,4-di-tert-butylphenoxide)
dimethylsilanediylbis(tetrahydroindenyl)zirconium monochloride mono(2,4-di-tert-butylphenoxide)
isopropylidenebisindenylzirconium monochloride mono(2,4-di-tert-butylphenoxide)
isopropylidenecyclopentadienyl-9-fluorenylzirconium monochloride mono(2,4-di-tert-butylphenoxide)
isopropylidenecyclopentadienylindenylzirconium monochloride mono(2,4-di-tert-butylphenoxide)
diphenylmethylidene(cyclopentadienyl)-(9-fluorenyl)zirconium monochloride mono(2,4-di-tert-butylphenoxide)
diphenylmethylidene(3-methylcyclopentadienyl)-(9-fluorenyl)zirconium monochloride mono(2,4-di-tert-butylphenoxide)
diphenylmethylidene(3-isopropylcyclopentadienyl)-(9-fluorenyl)zirconium monochloride mono(2,4-di-tert-butylphenoxide)
diphenylmethylidene(3-tert-butylcyclopentadienyl)-(9-fluorenyl)zirconium monochloride mono(2,4-di-tert-butylphenoxide)
dimethylsilanediylcyclopentadienyl-9-fluorenylzirconium monochloride mono(2,4-di-tert-butylphenoxide)
diphenylsilanediylcyclopentadienyl-9-fluorenylzirconium monochloride mono(2,4-di-tert-butylphenoxide)
dimethylsilanediylbis(2-methyl-4-(tert-butylphenylindenyl) zirconium monochloride mono(2,4-di-tert-butylphenoxide)
dimethylsilanediylbis(2-methyl-4-(4-methylphenylindenyl) zirconium monochloride mono(2,4-di-tert-butylphenoxide)
dimethylsilanediylbis(2-methyl-4-(4-ethylphenylindenyl) zirconium monochloride mono(2,4-di-tert-butylphenoxide)
dimethylsilanediylbis(2-methyl-4-(4-trifluoromethylphenylindenyl)zirconium monochloride mono(2,4-di-tert-butylphenoxide)
dimethylsilanediylbis(2-methyl-4-(4-methoxyphenylindenyl)zirconium monochloride mono(2,4-di-tert-butylphenoxide)
dimethylsilanediylbis(2-ethyl-4-(4-tert-butylphenylindenyl) zirconium monochloride mono(2,4-di-tert-butylphenoxide)
dimethylsilanediylbis(2-ethyl-4-(4-ethylphenylindenyl)zirconium monochloride mono(2,4-di-tert-butylphenoxide)
dimethylsilanediylbis(2-ethyl-4-(4-trifluoromethylphenylindenyl)zirconium monochloride mono(2,4-di-tert-butylphenoxide)
dimethylsilanediylbis(2-ethyl-4-(4-methoxyphenylindenyl) zirconium monochloride mono(2,4-di-tert-butylphenoxide)
dimethylsilanediylbis(2-methyl-4-(4'-tert-butylphenyl)indenyl)zirconium monochloride mono(2,4-di-tert-butylphenoxide)
dimethylsilanediylbis(2-methyl-4-(3',5'-di-tert-butylphenyl) indenyl)zirconium monochloride mono(2,4-di-tert-butylphenoxide)
methylidenebis(2-methyl-4-(4'-tert-butylphenyl)indenyl) zirconium monochloride mono(2,4-di-tert-butylphenoxide)
isopropylidenebis(2-methyl-4-(4'-tert-butylphenyl)indenyl) zirconium monochloride mono(2,4-di-tert-butylphenoxide)
dimethylsilanediylbis(2-methyl-4-(4'-methylphenyl)indenyl)zirconium monochloride mono(2,4-di-tert-butylphenoxide)
dimethylsilanediylbis(2-methyl-4-(4'-ethylphenyl)indenyl) zirconium monochloride mono(2,4-di-tert-butylphenoxide)
dimethylsilanediylbis(2-methyl-4-(4'-n-propylphenyl)indenyl)zirconium monochloride mono(2,4-di-tert-butylphenoxide)
dimethylsilanediylbis(2-methyl-4-(4'-isopropylphenyl)indenyl)zirconium monochloride mono(2,4-di-tert-butylphenoxide)
dimethylsilanediylbis(2-methyl-4-(4'-n-butylphenyl)indenyl)zirconium monochloride mono(2,4-di-tert-butylphenoxide)
dimethylsilanediylbis(2-methyl-4-(4'-hexylphenyl)indenyl) zirconium monochloride mono(2,4-di-tert-butylphenoxide)
dimethylsilanediylbis(2-methyl-4-(4'-sec-butylphenyl)indenyl)zirconium monochloride mono(2,4-di-tert-butylphenoxide)
dimethylsilanediylbis(2-ethyl-4-phenyl)indenyl)zirconium monochloride mono(2,4-di-tert-butylphenoxide)
dimethylsilanediylbis(2-ethyl-4-(4'-methylphenyl)indenyl) zirconium monochloride mono(2,4-di-tert-butylphenoxide)
dimethylsilanediylbis(2-ethyl-4-(4'-ethylphenyl)indenyl) zirconium monochloride mono(2,4-di-tert-butylphenoxide)
dimethylsilanediylbis(2-ethyl-4-(4'-n-propylphenyl)indenyl)zirconium monochloride mono(2,4-di-tert-butylphenoxide)
dimethylsilanediylbis(2-ethyl-4-(4'-isopropylphenyl)indenyl)zirconium monochloride mono(2,4-di-tert-butylphenoxide)
dimethylsilanediylbis(2-ethyl-4-(4'-n-butylphenyl)indenyl) zirconium monochloride mono(2,4-di-tert-butylphenoxide)

dimethylsilanediylbis(2-ethyl-4-(4'-hexylphenyl)indenyl)zirconium monochloride mono(2,4-di-tert-butylphenoxide)

dimethylsilanediylbis(2-ethyl-4-(4'-pentylphenyl)indenyl)zirconium monochloride mono(2,4-di-tert-butylphenoxide)

dimethylsilanediylbis(2-ethyl-4-(4'-cyclohexylphenyl)indenyl)zirconium monochloride mono(2,4-di-tert-butylphenoxide)

dimethylsilanediylbis(2-ethyl-4-(4'-sec-butylphenyl)indenyl)zirconium monochloride mono(2,4-di-tert-butylphenoxide)

dimethylsilanediylbis(2-ethyl-4-(4'-tert-butylphenyl)indenyl)zirconium monochloride mono(2,4-di-tert-butylphenoxide)

dimethylsilanediylbis(2-ethyl-4-(3',5'-di-tert-butylphenyl)indenyl)zirconium monochloride mono(2,4-di-tert-butylphenoxide)

methylidenebis(2-ethyl-4-(4'-tert-butylphenyl)indenyl)zirconium monochloride mono(2,4-di-tert-butylphenoxide)

isopropylidenebis(2-ethyl-4-(4'-tert-butylphenyl)indenyl)zirconium monochloride mono(2,4-di-tert-butylphenoxide)

dimethylsilanediylbis(2-n-propyl-4-phenyl)indenyl)zirconium monochloride mono(2,4-di-tert-butylphenoxide)

dimethylsilanediylbis(2-n-propyl-4-(4'-methylphenyl)indenyl)zirconium monochloride mono(2,4-di-tert-butylphenoxide)

dimethylsilanediylbis(2-n-propyl-4-(4'-ethylphenyl)indenyl)zirconium monochloride mono(2,4-di-tert-butylphenoxide)

dimethylsilanediylbis(2-n-propyl-4-(4'-n-propylphenyl)indenyl)zirconium monochloride mono(2,4-di-tert-butylphenoxide)

dimethylsilanediylbis(2-n-propyl-4-(4'-isopropylphenyl)indenyl)zirconium monochloride mono(2,4-di-tert-butylphenoxide)

dimethylsilanediylbis(2-n-propyl-4-(4'-n-butylphenyl)indenyl)zirconium monochloride mono(2,4-di-tert-butylphenoxide)

dimethylsilanediylbis(2-n-propyl-4-(4'-hexylphenyl)indenyl)zirconium monochloride mono(2,4-di-tert-butylphenoxide)

dimethylsilanediylbis(2-n-propyl-4-(4'-cyclohexylphenyl)indenyl)zirconium monochloride mono(2,4-di-tert-butylphenoxide)

dimethylsilanediylbis(2-n-propyl-4-(4'-sec-butylphenyl)indenyl)zirconium monochloride mono(2,4-di-tert-butylphenoxide)

dimethylsilanediylbis(2-n-propyl-4-(4'-tert-butylphenyl)indenyl)zirconium monochloride mono(2,4-di-tert-butylphenoxide)

dimethylsilanediylbis(2-n-propyl-4-(3',5'-di-tert-butylphenyl)indenyl)zirconium monochloride mono(2,4-di-tert-butylphenoxide)

methylidenebis(2-n-propyl-4-(4'-tert-butylphenyl)indenyl)zirconium monochloride mono(2,4-di-tert-butylphenoxide)

isopropylidenebis(2-n-propyl-4-(4'-tert-butylphenyl)indenyl)zirconium monochloride mono(2,4-di-tert-butylphenoxide)

dimethylsilanediylbis(2-n-butyl-4-phenyl)indenyl)zirconium monochloride mono(2,4-di-tert-butylphenoxide)

dimethylsilanediylbis(2-n-butyl-4-(4'-methylphenyl)indenyl)zirconium monochloride mono(2,4-di-tert-butylphenoxide)

dimethylsilanediylbis(2-n-butyl-4-(4'-ethylphenyl)indenyl)zirconium monochloride mono(2,4-di-tert-butylphenoxide)

dimethylsilanediylbis(2-n-butyl-4-(4'-n-propylphenyl)indenyl)zirconium monochloride mono(2,4-di-tert-butylphenoxide)

dimethylsilanediylbis(2-n-butyl-4-(4'-isopropylphenyl)indenyl)zirconium monochloride mono(2,4-di-tert-butylphenoxide)

dimethylsilanediylbis(2-n-butyl-4-(4'-n-butylphenyl)indenyl)zirconium monochloride mono(2,4-di-tert-butylphenoxide)

dimethylsilanediylbis(2-n-butyl-4-(4'-hexylphenyl)indenyl)zirconium monochloride mono(2,4-di-tert-butylphenoxide)

dimethylsilanediylbis(2-n-butyl-4-(4'-cyclohexylphenyl)indenyl)zirconium monochloride mono(2,4-di-tert-butylphenoxide)

dimethylsilanediylbis(2-n-butyl-4-(4'-sec-butylphenyl)indenyl)zirconium monochloride mono(2,4-di-tert-butylphenoxide)

dimethylsilanediylbis(2-n-butyl-4-(4'-tert-butylphenyl)indenyl)zirconium monochloride mono(2,4-di-tert-butylphenoxide)

dimethylsilanediylbis(2-hexyl-4-phenyl)indenyl)zirconium monochloride mono(2,4-di-tert-butylphenoxide)

dimethylsilanediylbis(2-hexyl-4-(4'-methylphenyl)indenyl)zirconium monochloride mono(2,4-di-tert-butylphenoxide)

dimethylsilanediylbis(2-hexyl-4-(4'-ethylphenyl)indenyl)zirconium monochloride mono(2,4-di-tert-butylphenoxide)

dimethylsilanediylbis(2-hexyl-4-(4'-n-propylphenyl)indenyl)zirconium monochloride mono(2,4-di-tert-butylphenoxide)

dimethylsilanediylbis(2-hexyl-4-(4'-isopropylphenyl)indenyl)zirconium monochloride mono(2,4-di-tert-butylphenoxide)

dimethylsilanediylbis(2-hexyl-4-(4'-n-butylphenyl)indenyl)zirconium monochloride mono(2,4-di-tert-butylphenoxide)

dimethylsilanediylbis(2-hexyl-4-(4'-hexylphenyl)indenyl)zirconium monochloride mono(2,4-di-tert-butylphenoxide)

dimethylsilanediylbis(2-hexyl-4-(4'-cyclohexylphenyl)indenyl)zirconium monochloride mono(2,4-di-tert-butylphenoxide)

dimethylsilanediylbis(2-hexyl-4-(4'-sec-butylphenyl)indenyl)zirconium monochloride mono(2,4-di-tert-butylphenoxide)

dimethylsilanediylbis(2-hexyl-4-(4'-tert-butylphenyl)indenyl)zirconium monochloride mono(2,4-di-tert-butylphenoxide)

dimethylgermanediylbis(2-ethyl-4-(4'-tert-butylphenyl)indenyl)zirconium monochloride mono(2,4-di-tert-butylphenoxide)

dimethylgermanediylbis(2-methyl-4-(4'-tert-butylphenyl)indenyl)zirconium monochloride mono(2,4-di-tert-butylphenoxide)

ethylidenebis(2-ethyl-4-phenyl)indenyl)zirconium monochloride mono(2,4-di-tert-butylphenoxide)

ethylidenebis(2-ethyl-4-(4'-tert-butylphenyl)indenyl)zirconium monochloride mono(2,4-di-tert-butylphenoxide)

ethylidenebis(2-n-propyl-4-(4'-tert-butylphenyl)indenyl)zirconium monochloride mono(2,4-di-tert-butylphenoxide)

ethylidenebis(2-methyl-4-(4'-tert-butylphenyl)indenyl)zirconium monochloride mono(2,4-di-tert-butylphenoxide)

methylethylidenebis(2-ethyl-4-(4'-tert-butylphenyl)indenyl) zirconium monochloride mono(2,4-di-tert-butylphenoxide)
dimethylsilanediyl(2-methylazapentalene)(2-methylindenyl)zirconium monochloride mono(2,4-di-tert-butylphenoxide)
dimethylsilanediyl(2-methylazapentalene)(2-methyl-4-phenylindenyl)zirconium monochloride mono(2,4-di-tert-butylphenoxide)
dimethylsilanediyl(2-methylazapentalene)(2-methyl-4,5-benzoindenyl)zirconium monochloride mono(2,4-di-tert-butylphenoxide)
dimethylsilanediyl(2-methylazapentalene)(2-ethyl-4-(4'-tert-butylphenylindenyl)zirconium monochloride mono(2,4-di-tert-butylphenoxide)
Dimethylsilanediyl(2-methylazapentalene)(2-methyl-4-(4'-tert-butyl-phenyl)indenyl)zirconium monochloride mono(2,4-di-tert-butylphenoxide)
dimethylsilanediyl(2-methylazapentalene)(2-n-propyl-4-(4'-tert-butylphenyl)indenyl)zirconium monochloride mono(2,4-di-tert-butylphenoxide)
dimethylsilanediyl(2-ethylazapentalene)(2-methyl-4-phenylindenyl) zirconium monochloride mono(2,4-di-tert-butylphenoxide)
dimethylsilanediyl(2-ethylazapentalene)(2-methyl-4-phenylindenyl) zirconium monochloride mono(2,4-di-tert-butylphenoxide)
dimethylsilanediyl(2-ethylazapentalene)(2-methyl-4,5-benzoindenyl)zirconium monochloride mono(2,4-di-tert-butylphenoxide)
dimethylsilanediyl(2-ethylazapentalene)(2-ethyl-4-(4'-tert-butylphenylindenyl)zirconium monochloride mono(2,4-di-tert-butylphenoxide)
dimethylsilanediyl(2-ethylazapentalene)(2-methyl-4-(4'-tert-butylphenyl)indenyl)zirconium monochloride mono(2,4-di-tert-butylphenoxide)
dimethylsilanediyl(2-ethylazapentalene)(2-n-propyl-4-(4'-tert-butylphenyl)indenyl)zirconium monochloride mono(2,4-di-tert-butylphenoxide)
dimethylsilanediyl(2-methylthiapentalene)(2-methylindenyl)zirconium monochloride mono(2,4-di-tert-butylphenoxide)
dimethylsilanediyl(2-methylthiapentalene)(2-methyl-4-phenylindenyl)zirconium monochloride mono(2,4-di-tert-butylphenoxide)
dimethylsilanediyl(2-methylthiapentalene)(2-methyl-4,5-benzoindenyl)zirconium monochloride mono(2,4-di-tert-butylphenoxide)
dimethylsilanediyl(2-methylthiapentalene)(2-ethyl-4-(4'-tert-butylphenyl)indenyl)zirconium monochloride mono(2,4-di-tert-butylphenoxide)
dimethylsilanediyl(2-methylthiapentalene)(2-n-propyl-4-(4'-tert-butylphenyl)indenyl)zirconium monochloride mono(2,4-di-tert-butylphenoxide)
dimethylsilanediyl(2-ethylthiapentalene)(2-methylindenyl) zirconium monochloride mono(2,4-di-tert-butylphenoxide)
dimethylsilanediyl(2-ethylthiapentalene)(2-methyl-4-phenylindenyl)zirconium monochloride mono(2,4-di-tert-butylphenoxide)
dimethylsilanediyl(2-ethylthiapentalene)(2-methyl-4,5-benzoindenyl)zirconium monochloride mono(2,4-di-tert-butylphenoxide)
Dimethylsilanediyl(2-ethylthiapentalene)(2-ethyl-4-(4'-tert-butylphenyl)indenyl)zirconium monochloride mono(2,4-di-tert-butylphenoxide)
dimethylsilanediyl(2-ethylthiapentalene)(2-n-propyl-4-(4'-tert-butylphenyl)indenyl)zirconium monochloride mono(2,4-di-tert-butylphenoxide).

Further examples of metallocenes according to the present invention are metallocenes from the above list in which the zirconium fragment "-zirconium monochloride mono(2,4-di-tert-butylphenoxide)" is replaced by zirconium monochloride mono(2,6-di-tert-butylphenoxide)
zirconium monochloride mono(3,5-di-tert-butylphenoxide)
zirconium monochloride mono(2,6-di-sec-butylphenoxide)
zirconium monochloride mono(2,4-di-methylphenoxide)
zirconium monochloride mono(2,3-di-methylphenoxide)
zirconium monochloride mono(2,5-di-methylphenoxide)
zirconium monochloride mono(2,6-di-methylphenoxide)
zirconium monochloride mono(3,4-di-methylphenoxide)
zirconium monochloride mono(3,5-di-methylphenoxide)
zirconium monochloride monophenoxide
zirconium monochloride mono(2-methylphenoxide)
zirconium monochloride mono(3-methylphenoxide)
zirconium monochloride mono(4-methylphenoxide)
zirconium monochloride mono(2-ethylphenoxide)
zirconium monochloride mono(3-ethylphenoxide)
zirconium monochloride mono(4-ethylphenoxide)
zirconium monochloride mono(2-sec-butylphenoxide)
zirconium monochloride mono(2-tert-butylphenoxide)
zirconium monochloride mono(3-tert-butylphenoxide)
zirconium monochloride mono(4-sec-butylphenoxide)
zirconium monochloride mono(4-tert-butylphenoxide)
zirconium monochloride mono(2-isopropyl-5-methylphenoxide)
zirconium monochloride mono(4-isopropyl-3-methylphenoxide)
zirconium monochloride mono(5-isopropyl-2-methylphenoxide)
zirconium monochloride mono(5-isopropyl-3-methylphenoxide)
zirconium monochloride mono(2,4-bis(2-methyl-2-butyl)phenoxide)
zirconium monochloride mono(2,6-di-tert-butyl-4-methylphenoxide)
zirconium monochloride mono(4-nonylphenoxide)
zirconium monochloride mono(isopropylphenoxide)
zirconium monochloride mono(propylphenoxide)
zirconium monochloride mono(trimethylphenoxide)
zirconium monochloride mono(tert-butyl-methylphenoxide)
zirconium monochloride mono(2-tert-butyl-4-ethylphenoxide)
zirconium monochloride mono(2,6-diisopropylphenoxide)
zirconium monochloride mono(4-octylphenoxide)
zirconium monochloride mono(2,6-di-tert-butyl-4-ethylphenoxide)
zirconium monochloride mono(1-naphtholate)
zirconium monochloride mono(2-naphtholate)
zirconium monochloride mono(2-phenylphenoxide)
zirconium monochloride mono(tert-butoxide)
zirconium monochloride mono(N-methylanilide)
zirconium monochloride mono(2-tert-butylanilide)
zirconium monochloride mono(tert-butylamide)
zirconium monochloride mono(di-isopropylamide)
zirconium monochloride monomethyl
zirconium monochloride monobenzyl
zirconium monochloride mononeopentyl.

The present invention further provides an industrially implementable process for the preparation of compounds of the formulae (I) and (II).

The synthesis of dicyclopentadienylzirconium 2,6-di-tert-butylphenoxide monochloride and dicyclopentadienylzirconium 2,6-diisopropylphenoxide monochloride is described in the literature (T. Repo et al., J. Organomet. Chem. 541 (1997), 363):

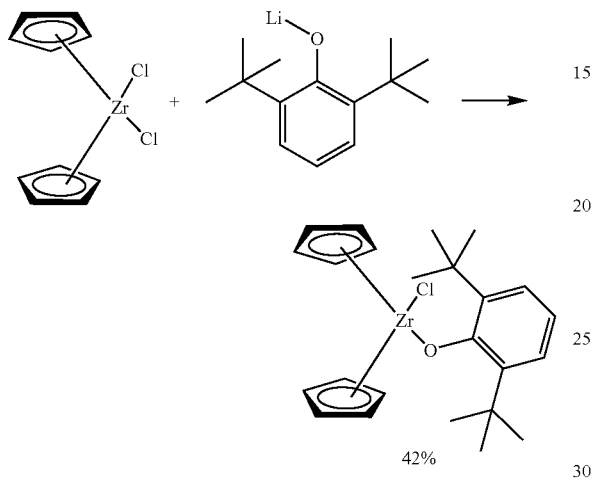

In the process described, the reaction is carried out at low temperatures (−78° C.), which is complicated and costly on an industrial scale; in addition, the yield obtained is only adequate.

It has now surprisingly been found that the preparation of the metallocenes of the formulae (I) and (II) can be carried out in good yields when metallocene halides are reacted with salts of the formula $M^1$—Y—$R^3$ in an inert solvent or solvent mixture at from 0° C. to 200° C., preferably from 60° C. to 110° C.:

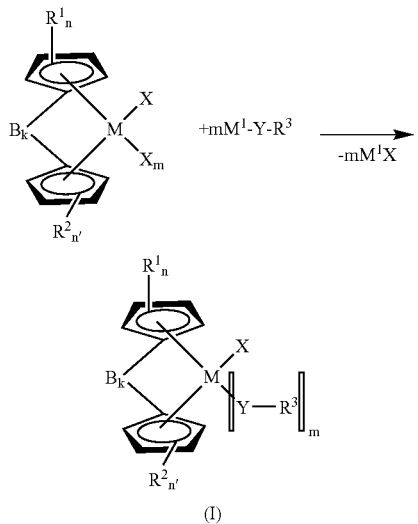

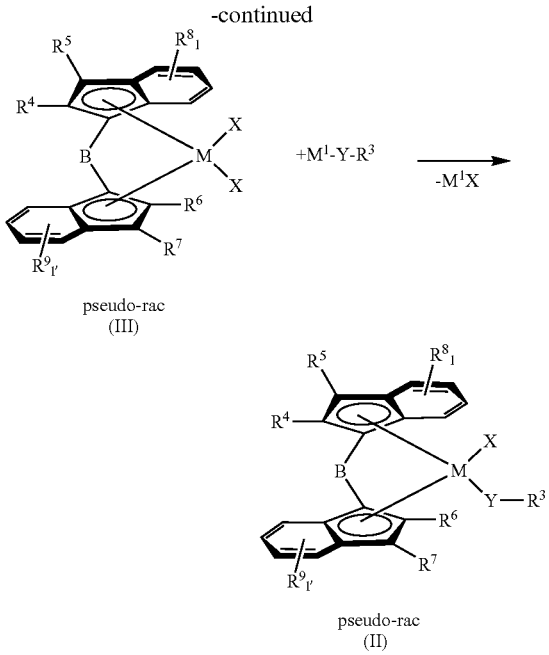

Here, $M^1$ is a cation or cation fragment such as Li, Na, K, MgCl, MgBr, MgI and the other symbols are as defined above.

The metallocenes used in the process are preferably metallocene dichlorides of the formula III as are described in the following documents: EP 0485823, EP 0549900, EP 0576970, WO 98/22486, WO 98/40331.

The compound $M^1$—Y—$R^3$ can be prepared by deprotonation of the compound H—Y—$R^3$ using a suitable base, for example butyllithium, methyllithium, sodium hydride, potassium hydride, sodium, potassium or Grignard compounds, in an inert solvent or solvent mixture.

Nonlimiting examples of suitable solvents are hydrocarbons which may be halogenated, for example benzene, toluene, xylene, mesitylene, ethylbenzene, chlorobenzene, dichlorobenzene, fluorobenzene, decalin, tetralin, pentane, hexane, cyclohexane, ethers such as diethyl ether, di-n-butyl ether, MTBE, THF, DME, anisole, triglyme, dioxane, amides such as DMF, dimethylacetamide, NMP, sulfoxides such as DMSO, phosphoramides such as hexamethylphosphoramide, urea derivatives such as DMPU, ketones such as acetone, ethyl methyl ketone, esters such as ethyl acetate, nitriles such as acetonitrile and also any mixtures of these substances. Preference is given to solvents or solvent mixtures in which the subsequent reaction with the metallocene dichloride can also be carried out. Nonlimiting examples of such solvents are toluene, hexane, heptane, xylene, tetrahydrofuran (THF), dimethoxyethane (DME), toluene/THF, heptane/DME and toluene/DME.

The compounds of the H—Y—$R^3$ type are preferably alcohols, phenols, primary and secondary amines or primary and secondary anilines. Preferably, compounds of the H—Y—$R^3$ type contain only one functional group H—Y and the radical $R^3$ is as defined above.

Illustrative but nonlimiting examples of compounds of the formula H—Y—$R^3$ which can be used for the purposes of the present invention are:

2,4-di-tert-butylphenol; 2,6-di-tert-butylphenol; 3,5-di-tert-butylphenol; 2,6-di-sec-butylphenol; 2,4-dimethylphenol; 2,3-dimethylphenol; 2,5-dimethylphenol; 2,6-dimethylphenol; 3,4-dimethylphenol; 3,5-dimethylphenol; phenol; 2-methylphenol; 3-methylphenol; 4-methylphenol; 2-ethylphenol; 3-ethylphenol; 4-ethylphenol; 2-sec-butylphenol; 2-tert-butylphenol; 3-tert-butylphenol; 4-sec-butylphenol; 4-tert-butylphenol; 2-isopropyl-5-methylphenol; 4-isopropyl-3-methylphenol; 5-isopropyl-2-methylphenol; 5-isopropyl-3-methylphenol; 2,4-bis(2-methyl-2-butyl)phenol; 2,6-di-tert-butyl-4-methylphenol; 4-nonylphenol; 2-isopropylphenol; 3-isopropylphenol; 4-isopropylphenol; 2-propylphenol; 4-propylphenol; 2,3,5-trimethylphenol; 2,3,6-trimethylphenol; 2,4,6-trimethylphenol; 3,4,5-trimethylphenol; 2-tert-butyl-4-methylphenol; 2-tert-butyl-5-methylphenol; 2-tert-butyl-6-methylphenol; 4-(2-methyl-2-butyl)-phenol; 2-tert-butyl-4-ethylphenol; 2,6-diisopropylphenol; 4-octylphenol; 4-(1,1,3,3-tetramethylbutyl)phenol; 2,6-di-tert-butyl-4-ethylphenol; 4-sec-butyl-2,6-di-tert-butylphenol; 4-dodecylphenol; 2,4,6-tri-tert-butylphenol; 3-(pentadecyl)phenol; 2-methyl-1-naphthol;

1-naphthol; 2-naphthol; 1-acenaphthenol; 2-hydroxybiphenyl; 3-hydroxybiphenyl; 4-hydroxybiphenyl; hydroxypyridines; hydroxyquinolines; 2-hydroxycarbazoles; hydroxyquinaldines; 8-hydroxyquinazoline; 2-hydroxyquinoxaline; 2-hydroxydibenzofuran; 2-hydroxydiphenylmethane, 1-hydroxyisoquinolines, 5,6,7,8-tetrahydro-1-naphthol; methanol; ethanol; propanol; isopropanol; butanol; tert-butanol; isobutanol; 2-butanol; hexanol; cyclohexanol; octadecanol; benzyl alcohol; 2-methylbenzyl alcohol; 3-methylbenzyl alcohol; 4-methylbenzyl alcohol; aniline; N-methylaniline; o-toluidine; 2,3-dimethylaniline; 2,4-dimethylaniline; 2,5-dimethylaniline; 2,6-dimethylaniline; N-ethylaniline; 2-ethylaniline; N-ethyl-o-toluidine; N-ethyl-m-toluidine; 2-isopropylaniline; 2-propylaniline; 2,4,6-trimethylaniline; 2-tert-butylaniline; 2,3-dimethyl-N-ethylaniline; isopropylamine; tert-butylamine; diethylamine; N-methylisopropylamine; N-ethylisopropylamine; diisopropylamine; N-methyl-tert-butylamine; N-benzylmethylamine; 2-methylbenzylamine; 3-methylbenzylamine; 4-methylbenzylamine; 1-phenylethylamine and 2-phenylethylamine.

The process of the present invention is generally carried out in a temperature range from 0° C. to +200° C., preferably from 40° C. to 140° C., particularly preferably from 60° C. to 110° C.

The molar ratio of the reagent $M^1$—Y—$R^3$ to metallocene halide, in particular to metallocene dichloride (e.g. of the formula III), is generally from 5:1 to 0.8:1, preferably from 2:1 to 0.9:1.

The concentration of metallocene dichloride (e.g. of the formula III) or of reagent $M^1$—Y—$R^3$ in the reaction mixture is generally in the range from 0.001 mol/l to 8 mol/l, preferably from 0.01 to 3 mol/l, particularly preferably from 0.05 mol/l to 2 mol/l.

The duration of the reaction of metallocene dichloride (e.g. of the formula III) with the reagent $M^1$—Y—$R^3$ is generally in the range from 5 minutes to 1 week, preferably from 15 minutes to 48 hours.

Furthermore, monoaryloxymonochlorozirconocenes of the formula (II), in particular, can also be prepared by the method described in the German Patent Application 199 12576.7 of Mar. 19, 1999, whose disclosure is hereby incorporated by reference into the present description.

The novel metallocenes of the formulae I and II are highly active catalyst components for olefin polymerization. Depending on the substitution pattern of the ligands, the metallocenes can be obtained as a mixture of isomers. The metallocenes are preferably used in isomerically pure form for the polymerization.

Preference is given to using the pseudo-rac isomers of the metallocenes of the formula II.

The novel metallocenes of the formulae I and II are, in particular, suitable as constituents of catalyst systems for preparing polyolefins by polymerization of at least one olefin in the presence of a catalyst comprising at least one cocatalyst and at least one metallocene. For the purposes of the present invention, the term polymerization encompasses both homopolymerization and copolymerization.

The novel metallocenes of the formulae I and II, in particular of the formula II, can be used for the polymerization of one or more olefins of the formula $R^\alpha$—CH=CH—$R^\beta$, where $R^\alpha$ and $R^\beta$ are identical or different and are each a hydrogen atom or a hydrocarbon having from 1 to 20 carbon atoms, in particular from 1 to 10 carbon atoms, and $R^\alpha$ and $R^\beta$ together with the atoms connecting them can form one or more rings. Examples of such olefins are 1-olefins having 2–40 carbon atoms, preferably from 2 to 10 carbon atoms, for example ethene, propene, 1-butene, 1-pentene, 1-hexene, 4-methyl-1-pentene or 1-octene, styrene, dienes such as 1,3-butadiene, 1,4-hexadiene, vinylnorbornene, norbornadiene, ethylnorbornadiene and cyclic olefins such as norbornene, tetracyclododecene or methylnorbornene. Preference is given to homopolymerizing ethylene or propylene or copolymerizing ethylene with one or more cyclic olefins, e.g. norbornene, and/or one or more dienes having from 4 to 20 carbon atoms, e.g. 1,3-butadiene or 1,4-hexadiene. Examples of such copolymers are ethylene/norbornene copolymers, ethylene/propylene copolymers and ethylene/propylene/1,4-hexadiene copolymers.

The polymerization is carried out at from −60 to 300° C. preferably from 50 to 200° C., very particularly preferably 50–80° C. The pressure is from 0.5 to 2000 bar, preferably from 5 to 64 bar.

The polymerization can be carried out in solution, in bulk, in suspension or in the gas phase, continuously or batchwise and in one or more stages. A preferred embodiment is gas-phase and bulk polymerization.

The catalyst used preferably comprises one of the metallocene compounds of the present invention. It is also possible to use mixtures of two or more metallocene compounds, e.g. for preparing polyolefins having a broad or multimodal molar mass distribution.

The cocatalyst which together with a novel metallocene of the formula I or II forms the catalyst system comprises at least one compound of the aluminoxane type or a Lewis acid or an ionic compound which reacts with a metallocene to convert it into a cationic compound.

As aluminoxane, preference is given to using a compound of the formula (VII)

$$(R\ AlO)_n \tag{VII}$$

Further suitable aluminoxanes may be, for example, cyclic as in formula (VI)

$$\left[\begin{array}{c} R \\ | \\ -O-Al- \end{array}\right]_{p+2} \quad (VI)$$

or linear as in formula (IV)

$$\begin{array}{c} R \\ \diagdown \\ R \diagup \end{array} Al-O-\left[\begin{array}{c} R \\ | \\ Al-O \end{array}\right]_p Al \begin{array}{c} \diagup R \\ \diagdown R \end{array} \quad (IV)$$

or of the cluster type as in formula (V)

(V)

Such aluminoxanes are described, for example, in JACS 117 (1995), 6465–74, Organometallics 13 (1994), 2957–2969.

The radicals R in the formulae (IV), (V), (VI) and (VII) may be identical or different and may each be a $C_1$–$C_{20}$-hydrocarbon group such as a $C_1$–$C_6$-alkyl group, a $C_6$–$C_{18}$-aryl group, benzyl or hydrogen and p is an integer from 2 to 50, preferably from 10 to 35.

The radicals R are preferably identical and are methyl, isobutyl, n-butyl, phenyl or benzyl, particularly preferably methyl. If the radicals R are different, they are preferably methyl and hydrogen, methyl and isobutyl or methyl and n-butyl, with hydrogen or isobutyl or n-butyl preferably being present in a proportion of 0.01–40% (number of radicals R).

The aluminoxane can be prepared in various ways by known methods. One of the methods is, for example, to react an aluminum-hydrocarbon compound and/or a hydridoaluminum-hydrocarbon compound with water (gaseous, solid, liquid or bound—for example as water of crystallization) in an inert solvent (e.g. toluene).

To prepare an aluminoxane having different alkyl groups R, two different trialkylaluminums ($AlR_3$+$AlR'_3$) corresponding to the desired composition and reactivity are reacted with water (cf. S. Pasynkiewicz, Polyhedron 9 (1990) 429 and EP-A-0,302,424).

Regardless of the method of preparation, all aluminoxane solutions have a varying content of unreacted aluminum starting compound which is present in free form or as adduct.

As Lewis acid, preference is given to using at least one organoboron or organoaluminum compound containing $C_1$–$C_{20}$-groups such as branched or unbranched alkyl or haloalkyl, e.g. methyl, propyl, isopropyl, isobutyl or trifluoromethyl, unsaturated groups such as aryl or haloaryl, e.g. phenyl, tolyl, benzyl groups, p-fluorophenyl, 3,5-difluorophenyl, pentachlorophenyl, pentafluorophenyl, 3,4,5-trifluorophenyl and 3,5-di(trifluoromethyl)phenyl.

Examples of Lewis acids are trimethylaluminum, triethylaluminum, triisobutylaluminum, tributylaluminum, trifluoroborane, triphenylborane, tris(4-fluorophenyl)borane, tris(3,5-difluorophenyl)borane, tris(4-fluoromethylphenyl)borane, tris(pentafluorophenyl)borane, tris(tolyl)borane, tris(3,5-dimethylphenyl)borane, tris(3,5-difluorophenyl)borane, $[(C_6F_5)_2BO]_2Al$—Me, $[(C_6F_5)_2BO]_3Al$ and/or tris(3,4,5-trifluorophenyl)borane. Particular preference is given to tris(pentafluorophenyl)borane.

As ionic cocatalysts, preference is given to using compounds containing a noncoordinating anion, for example tetrakis(pentafluorophenyl)borates, tetraphenylborates, $SbF_6$—, $CF_3SO_3$— or $ClO_4$—.

Cationic counterions used are protonated Lewis bases such as methylamine, aniline, dimethylamine, diethylamine, N-methylaniline, diphenylamine, N,N-dimethylaniline, trimethylamine, triethylamine, tri-n-butylamine, methyldiphenylamine, pyridine, p-bromo-N,N-dimethylaniline, p-nitro-N,N-dimethylaniline, triethylphosphine, triphenylphosphine, diphenylphosphine, tetrahydrothiophene or the triphenylcarbenium cation.

Examples of such ionic compounds are
triethylammonium tetra(phenyl)borate,
tributylammonium tetra(phenyl)borate,
trimethylammonium tetra(tolyl)borate,
tributylammonium tetra(tolyl)borate,
tributylammonium tetra(pentafluorophenyl)borate,
tributylammonium tetra(pentafluorophenyl)aluminate,
tripropylammonium tetra(dimethylphenyl)borate,
tributylammonium tetra(trifluoromethylphenyl)borate,
tributylammonium tetra(4-fluorophenyl)borate,
N,N-dimethylanilinium tetra(phenyl)borate,
N,N-diethylanilinium tetra(phenyl)borate,
N,N-dimethylanilinium tetrakis(pentafluorophenyl)borate,
N,N-dimethylanilinium tetrakis(pentafluorophenyl)aluminate,
di(propyl)ammonium tetrakis(pentafluorophenyl)borate,
di(cyclohexyl)ammonium tetrakis(pentafluorophenyl)borate,
triphenylphosphonium tetrakis(phenyl)borate,
triethylphosphonium tetrakis(phenyl)borate,
diphenylphosphonium tetrakis(phenyl)borate,
tri(methylphenyl)phosphonium tetrakis(phenyl)borate,
tri(dimethylphenyl)phosphonium tetrakis(phenyl)borate,
triphenylcarbenium tetrakis(pentafluorophenyl)borate,
triphenylcarbenium tetrakis(pentafluorophenyl)aluminate,
triphenylcarbenium tetrakis(phenyl)aluminate,
ferrocenium tetrakis(pentafluorophenyl)borate and/or
ferrocenium tetrakis(pentafluorophenyl)aluminate.

Preference is given to triphenylcarbenium tetrakis(pentafluorophenyl)borate and/or
N,N-dimethylanilinium tetrakis(pentafluorophenyl)borate.

It is also possible to use mixtures of at least one Lewis acid and at least one ionic compound.

Further suitable cocatalyst components are borane or carborane compounds such as
7,8-dicarbaundecaborane(13), undecahydrido-7,8-dimethyl-7,8-dicarbaundecaborane,
dodecahydrido-1-phenyl-1,3-dicarbanonaborane,
tri(butyl)ammonium undecahydrido-8-ethyl-7,9-dicarbaundecaborate,
4-carbanonaborane(14), bis(tri(butyl)ammonium)nonaborate,
bis(tri(butyl)ammonium) undecaborate,
bis(tri(butyl)ammonium) dodecaborate,
bis(tri(butyl)ammonium) decachlorodecaborate,
tri(butyl)ammonium 1-carbadecaborate,
tri(butyl)ammonium 1-carbadodecaborate,
tri(butyl)ammonium 1-trimethylsilyl-1-carbadecaborate,
tri(butyl)ammonium bis(nonahydrido-1,3-dicarbanonaborato)cobaltate(III), tri(butyl)ammonium
bis(undecahydrido-7,8-dicarbaundecaborato)ferrate(III).

Further cocatalysts which may be used in unsupported or supported form are the compounds mentioned in EP-A-0924223, DE-A-19622207, EP-A-0601830, EP-A-0824112, EP-A-0824113, WO 99/06414, EP-A-0811627 and DE-A-19804970.

The support component of the catalyst sytsem of the present invention can be any organic or inorganic, inert solid, in particular a porous support such as talc, inorganic oxides and finely divided polymer powders (e.g. polyolefins).

Suitable inorganic oxides are oxides of elements of groups 2, 3, 4, 5, 13, 14, 15 and 16 of the Periodic Table of the Elements. Examples of oxides preferred as supports include silicon dioxide, aluminum oxide and mixed oxides of the two elements and corresponding oxide mixtures. Other inorganic oxides which can be used alone or in combination with the last-named preferred oxidic supports are, for example, MgO, $ZrO_2$, $TiO_2$ or $B_2O_3$, to name only a few.

The support materials used have a specific surface area in the range from 10 to 1000 $m^2/g$, a pore volume in the range from 0.1 to 5 ml/g and a mean particle size of from 1 to 500 μm. Preference is given to supports having a specific surface area in the range from 50 to 500 $m^2/g$, a pore volume in the range from 0.5 to 3.5 ml/g and a mean particle size in the range from 5 to 350 μm. Particular preference is given to supports having a specific surface area in the range from 200 to 400 $m^2/g$, a pore volume in the range from 0.8 to 3.0 ml/g and a mean particle size of from 10 to 200 μm.

If the support material used naturally has a low moisture content or residual solvent content, dehydration or drying before use can be omitted. If this is not the case, for example when using silica gel as support material, dehydration or drying is advisable. Thermal dehydration or drying of the support material can be carried out under reduced pressure combined with inert gas blanketing (e.g. nitrogen). The drying temperature is in the range from 100 to 1000° C., preferably from 200 to 800° C. The parameter pressure is not critical in this case. The duration of the drying process can be from 1 to 24 hours. Shorter or longer drying times are possible, provided that equilibrium with the hydroxyl groups on the support surface can be established under the conditions selected, which normally requires from 4 to 8 hours.

Dehydration or drying of the support material can also be carried out by chemical means by reacting the adsorbed water and the hydroxyl groups on the surface with suitable passivating agents. The reaction with the passivating reagent enables the hydroxyl groups to be converted completely or partially into a form which leads to no negative interactions with the catalytically active centers. Suitable passivating agents are, for example, silicon halides and silanes, e.g. silicon tetrachloride, chlorotrimethylsilane, dimethylaminotrichlorosilane, or organometallic compounds of aluminum, boron and magnesium, for example trimethylaluminum, triethylaluminum, triisobutylaluminum, triethylborane, dibutylmagnesium. Chemical dehydration or passivation of the support material is carried out, for example, by reacting a suspension of the support material in the absence of air and moisture in a suitable solvent with the passivating reagent in pure form or in the form of a solution in a suitable solvent. Suitable solvents are, for example, aliphatic or aromatic hydrocarbons such as pentane, hexane, heptane, toluene or xylene. Passivation is carried out at from 25° C. to 120° C., preferably from 50 and 70° C. Higher and lower temperatures are possible. The reaction time is from 30 minutes to 20 hours, preferably from 1 to 5 hours. After the chemical dehydration has proceeded to completion, the support material is isolated by filtration under inert conditions, washed one or more times with suitable inert solvents as have been described above and subsequently dried in a stream of inert gas or under reduced pressure.

Organic support materials such as finely divided polyolefin powder (e.g. polyethylene, polypropylene or polystyrene) can also be used and should likewise be freed before use of adhering moisture, solvent residues or other impurities by appropriate purification and drying operations.

According to the present invention, the catalyst system is prepared by mixing at least one metallocene according to the present invention, at least one cocatalyst and at least one passivated support.

To prepare the supported catalyst system, at least one of the above-described metallocene components is brought into contact in a suitable solvent with at least one cocatalyst component, preferably so as to give a soluble reaction product, an adduct or a mixture. The preparation obtained in this way is then mixed with the dehydrated or passivated support material, the solvent is removed and the resulting supported metallocene catalyst system is dried in order to ensure that all or most of the solvent is removed from the pores of the support material. The supported catalyst is obtained as a free-flowing powder.

A process for preparing a free-flowing and possibly prepolymerized supported catalyst system comprises the following steps:

a) preparation of a metallocene/cocatalyst mixture in a suitable solvent or suspension medium, with the metallocene component preferably having one of the above-described structures,
b) application of the metallocene/cocatalyst mixture to a porous, preferably inorganic dehydrated support,
c) removal of the major part of solvent from the resulting mixture,
d) isolation of the supported catalyst system,
e) if desired, prepolymerization of the resulting supported catalyst system with one or more olefinic monomer(s) so as to give a prepolymerized supported catalyst system.

Preferred solvents for the preparation of the metallocene/cocatalyst mixture are hydrocarbons and hydrocarbon mixtures which are liquid at the reaction temperature selected and in which the individual components preferably dissolve. However, solubility of the individual components is not a prerequisite as long as it is ensured that the reaction product of metallocene and cocatalyst components is soluble in the solvent selected. Examples of suitable solvents include alkanes such as pentane, isopentane, hexane, heptane, octane and nonane; cycloalkanes such as cyclopentane and cyclohexane; and aromatics such as benzene, toluene, ethylbenzene and diethylbenzene. Very particular preference is given to toluene.

The amounts of aluminoxane and metallocene used in the preparation of the supported catalyst system can be varied within a wide range. Preference is given to a molar ratio of aluminum to transition metal in the metallocene of from 10:1 to 1000:1, very particularly preferably from 50:1 bis 500:1.

In the case of methylaluminoxane, preference is given to using 30% strength solutions in toluene; however, the use of 10% strength solutions is also possible.

For the preactivation, the metallocene in the form of a solid is dissolved in a solution of the aluminoxane in a suitable solvent. However, it is also possible to dissolve the metallocene separately in a suitable solvent and subsequently to combine this solution with the aluminoxane solution. Preference is given to using toluene.

The preactivation time is from 1 minute to 200 hours.

The preactivation can take place at room temperature (25° C.). The use of higher temperatures can in individual cases shorten the preactivation time required and effect an additional increase in activity. In this case, higher temperatures means a range from 50 to 100° C.

The preactivated solution or metallocene/cocatalyst mixture is subsequently combined with an inert support material, usually silica gel which is in the form of a dry powder or as a suspension in one of the abovementioned solvents. The support material is preferably used as powder. The order of addition is immaterial. The preactivated metallocene/cocatalyst solution or the metallocene/cocatalyst mixture can be added to the support material or else the support material can be added to the solution.

The volume of the preactivated solution or of the metallocene/cocatalyst mixture can exceed 100% of the total pore volume of the support material used or else can be up to 100% of the total pore volume.

The temperature at which the preactivated soluton or the metallocene/cocatalyst mixture is brought into contact with the support material can vary within a range from 0 to 100° C. However, lower or higher temperatures are also possible.

Subsequently, all or most of the solvent is removed from the supported catalyst system, with the mixture being able to be stirred and, if desired, also heated. Preferably, both the visible proportion of the solvent and also the proportion present in the pores of the support material are removed. Removal of the solvent can be carried out in a conventional manner using reduced pressure and/or flushing with inert gas. During the drying procedure, the mixture can be heated until the free solvent has been removed, which usually takes from 1 to 3 hours at a preferred temperature of from 30 to 60° C. The free solvent is the visible proportion of solvent in the mixture. For the purposes of the present invention, residual solvent is the proportion enclosed in the pores.

As an alternative to complete removal of the solvent, the supported catalyst system can be dried only to a particular residual solvent content, with the free solvent having been completely removed. The supported catalyst system can subsequently be washed with a low-boiling hydrocarbon such as pentane or hexane and dried again.

The supported catalyst system prepared can either be used directly for the polymerization of olefins or it can be prepolymerized with one or more olefinic monomers prior to use in a polymerization process. The procedure for the prepolymerization of supported catalyst systems is described, for example, in WO 94/28034.

As additives, it is possible to add a small amount of an olefin, preferably an a-olefin (for example a styrene or phenyldimethylvinylsilane) as activity-promoting component, or, for example, an antistatic, during or after the preparation of the supported catalyst system.

As antistatic, use is usually made of a mixture of a metal salt of Medialan acid, a metal salt of anthranilic acid and a polyamine. Such antistatics are described, for example, in EP-A-0,636,636.

The molar ratio of additive to metallocene compound (I) is preferably from 1:1000 to 1000:1, very particularly preferably from 1:20 to 20:1.

The present invention also provides a process for preparing a polyolefin by polymerization of one or more olefins in the presence of a catalyst system comprising at least one of the novel metallocenes of the formula I or II as transition metal component. For the purposes of the present invention, the term polymerization covers both homopolymerization and copolymerization.

Compared to the dihalo compounds, the novel compounds of the formulae (I) and (II) display at least equal, but sometimes higher, activities in the polymerization of olefins, and the polyolefins obtained display a reduction in the undesirable low molecular weight extractables content.

The catalyst system described can be used as sole catalyst component for the polymerization of olefins having from 2 to 20 carbon atoms, but is preferably used in combination with at least one alkyl compound of elements of main groups I to III of the Periodic Table, e.g. an aluminum alkyl, magnesium alkyl or lithium alkyl or an aluminoxane. The alkyl compound is added to the monomers or suspension medium and serves to purify the monomers of substances which could impair the catalyst activity. The amount of alkyl compound added depends on the quality of the monomers used.

As molar mass regulator and to increase the activity, hydrogen is added if necessary.

In the polymerization, the antistatic can be metered into the polymerization system either together with or separately from the catalyst system used.

The polymers prepared using the catalyst system comprising at least one of the novel metallocenes of the formulae (I) and/or (II) display a uniform particle morphology and contain no fines. No deposits in the reactor or caked material occur in the polymerization using the catalyst system.

The catalyst system gives polymers such as polypropylene having an extraordinarily high stereospecificity and regiospecificity.

The stereospecificity and regiospecificity of polymers, in particular polypropylene, are characterized, in particular, by the triad tacticity (TT) and the proportion of 2-1-inserted propene units (RI) which can be determined from the $^{13}$C-NMR spectra.

The $^{13}$C-NMR spectra are measured in a mixture of hexachlorobutadiene and $d_2$-tetrachloroethane at elevated temperature (365 K). All $^{13}$C-NMR spectra of the polypropylene samples measured are calibrated using the resonance signal of $d_2$-tetrachloroethane ($\delta$=73.81 ppm) as standard.

To determine the triad tacticity of the polypropylene, the methyl resonance signals in the $^{13}$C-NMR spectrum in the range from 23 to 16 ppm are examined; cf. J. C. Randall, Polymer Sequence Determination: Carbon-13 NMR Method, Academic Press New York 1978; A. Zambelli, P. Locatelli, G. Bajo, F. A. Bovey, Macromolucules 8 (1975), 687–689; H. N. Cheng, J. A. Ewen, Makromol. Chem. 190 (1989), 1931–1943. Three successive 1-2-inserted propene units whose methyl groups are located on the same side in the "Fischer projection" are designated as mm 25 triads ($\delta$=21.0 ppm to 22.0 ppm). If only the second methyl group of the three successive propene units points to the other side, this is referred to as an rr triad (δ=19.5 ppm to 20.3 ppm), and if only the third methyl group of the three successive propene units points to the other side, this is referred to as an mr-triad (δ=20.3 ppm to 21.0 ppm). The triad tacticity is calculated according to the following formula:

$$TT\ (\%)=mm/(mm+mr+rr)\cdot 100$$

If a propene unit is inserted inversely into the growing polymer chain, this is referred to as a 2-1-insertion; cf. T. Tsutsui, N. Ishimaru, A. Mizuno, A. Toyota, N. Kashiwa, Polymer 30, (1989), 1350–56. The following different structural arrangements are possible:

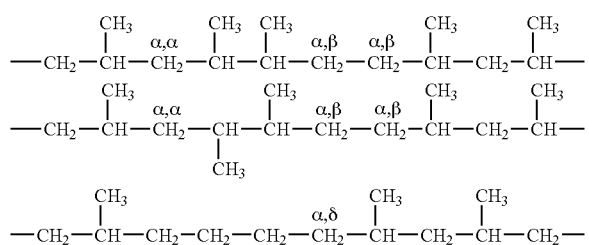

The proportion of 2-1-inserted propene units (RI) can be calculated according to the following formula:

$$RI(\%)=0.5 I\alpha,\beta (I\alpha,\alpha + I\alpha,\beta + I\alpha,\delta) \cdot 100,$$

where

Iα,α is the sum of the intensities of the resonance signals at δ=41.84, 42.92 and 46.22 ppm, Iα,β is the sum of the intensities of the resonance signals at δ=30.13, 32.12, 35.11 and 35.57 ppm and Iα,δ is the intensity of the resonance signal at δ 37.08 ppm.

The isotactic polypropylene which has been prepared using the catalyst system has a proportion of 2-1-inserted propene units RI<0.5% at a triad tacticity TT>98.0% and a melting point of >153° C., with $M_w/M_n$ of the polypropylene prepared according to the present invention being from 2.5 to 3.5.

The copolymers which can be prepared using the catalyst system have a significantly higher molar mass than those prepared according to the prior art. At the same time, such copolymers can be prepared with higher productivity at industrially feasible process parameters without deposit formation by using the catalyst system.

The polymers prepared by the process are suitable, in particular, for producing hard and rigid moldings having a good tensile strength, for example fibers, filaments, injection-molded parts, films, sheets or large hollow bodies (e.g. pipes).

The invention is illustrated by the nonrestrictive examples below.

General procedures: The preparation and handling of the organometallic compounds was carried out in the absence of air and moisture under protective argon gas (Schlenk technique or glove box). All solvents required were purged with argon and dried over molecular sieves before use.

EXAMPLE 1

Dimethylsilanediylbis(2-methyl-4,5-benzoindenyl) zirconium monochloride mono(2,4-di-tert-butylphenoxide) (1)

20.6 g (0.1 mol) of 2,4-di-tert-butylphenol in 200 ml of toluene/20 ml of THF were admixed at room temperature with 37.2 ml (0.1 mol) of a 20% strength solution of butyllithium in toluene. The mixture was stirred for another 1 hour at 60° C. At room temperature, 28.8 g (0.05 mol) of dimethylsilanediyl-bis(2-methyl-4,5-benzoindenyl)zirconium dichloride were added as a solid. The suspension was stirred for 3 hours at 100° C. and subsequently filtered hot through Celite. The filter cake was extracted 3 times with 100 ml each time of toluene (100° C.). After evaporating part of the solvent, the yellow solid which precipitated was filtered off and dried under reduced pressure. This gave 31.1 g (83%) of dimethylsilanediylbis(2-methyl-4,5-benzoindenyl)zirconium monochloride mono(2,4-di-tert-butylphenoxide) (1).

$^1$H-NMR (400 MHz, CDCl$_3$): 8.05 (dd, 1H), 7.75 (m, 2H), 7.65 (dd, 1H), 7.60 (1H), 7.5–7.15 (m, 6H), 7.1 (m, 1H), 7.0 (m, 1H), 6.85 (s, 1H), 6.8 (d, 1H), 6.65 (m, 1H), 5.45 (d, 1H), 2.82 (s, 3H), 2.45 (s, 3H), 1.45 (s, 3H), 1.35 (s, 3H), 1.25 (s, 9H), 0.95 (s, 9H).

Solubility Comparison:

50 mg of dimethylsilanediylbis(2-methyl-4,5-benzoindenyl)zirconium dichloride dissolved completely in 240 ml of toluene at room temperature (solubility about 0.36 mmol/l).

50 mg of compound (1) dissolved immediately in <5 ml of toluene at room temperature (solubility >13 mmol/l).

EXAMPLE 1a

Catalyst Preparation Using (1) and Polymerization:

35.1 mg (0.047 mmol) of (1) were stirred in 2.1 ml of 30% strength MAO solution in toluene (Al/Zr=215) for 60 minutes at room temperature. 2 g of SiO$_2$ (Grace XPO2107, pretreated at 140° C., 10 mbar, 10 hours) were subsequently added thereto and the mixture was stirred for a further 10 minutes. The solvent was removed in an oil pump vacuum.

A dry 2 l reactor was flushed first with nitrogen and subsequently with propylene and charged with 1.5 l of liquid propylene. 2 ml of TEA (20% strength in Varsol) were added thereto and the mixture was stirred for 15 minutes. Subsequently, the above catalyst system (0.886 g) resuspended in 20 ml of heptane was injected and rinsed in using 15 ml of heptane. The reaction mixture was heated to the polymerization temperature of 60° C. and polymerization was carried out for 1 hour. The polymerization was stopped by venting the remaining propylene. The polymer was dried in a vacuum drying oven, giving 470 g of polypropylene powder. The reactor displayed no deposits on the inner wall or stirrer. The catalyst activity was 0.53 kg of PP/g of catalyst x h.

COMPARATIVE EXAMPLE

Catalyst Preparation Using dimethylsilanediylbis(2-methyl-4,5-benzoindenyl) zirconium dichloride and polymerization 27.1 mg (0.047 mmol) of dimethylsilanediylbis(2-methyl-4,5-benzoindenyl)zirconium dichloride were stirred in 2.1 ml of 30% strength MAO solution in toluene (Al/Zr=215) for 60 minutes at room temperature. 2 g of SiO$_2$ (Grace XPO2107, pretreated at 140° C., 10 mbar, 10 hours) were subsequently added thereto and the mixture was stirred for a further 10 minutes. The solvent was removed in an oil pump vacuum.

A dry 2 l reactor was flushed first with nitrogen and subsequently with propylene and charged with 1.5 l of liquid propylene. 2 ml of TEA (20% strength in Varsol) were added thereto and the mixture was stirred for 15 minutes. Subsequently, the above catalyst system (0.897 g) resuspended in 20 ml of heptane was injected and rinsed in using 15 ml of heptane. The reaction mixture was heated to the polymerization temperature of 60° C. and polymerization was carried out for 1 hour. The polymerization was stopped by venting the remaining propylene. The polymer was dried in a vacuum drying oven, giving 410 g of polypropylene powder. The reactor displayed no deposits on the inner wall or stirrer. The catalyst activity was 0.46 kg of PP/g of catalyst x h.

EXAMPLE 2

Dimethylsilanediylbis(2-methylindenyl)zirconium monochloride mono(2,4-di-tert-butylphenoxide) (2)

1.03 g (5 mmol) of 2,4-di-tert-butylphenol in 10 ml of toluene/1 ml of THF were admixed at room temperature with 1.85 ml (5 mmol) of a 20% strength solution of butyllithium in toluene. The mixture was stirred for another 1 hour at 60° C. At room temperature, 1.19 g (2.5 mmol) of dimethylsilanediylbis-(2-methylindenyl)zirconium dichloride were added as a solid. The suspension was stirred for 2 hours at 60° C. and subsequently filtered hot through Celite. The filter cake was extracted 3 times with 10 ml each time of toluene (60° C.). After evaporation of part of the solvent, the yellow solid which precipitated was filtered off and dried under reduced pressure. This gave 0.87 g (53%) of dimethylsilanediylbis(2-methylindenyl)zirconium monochloride mono(2,4-di-tert-butylphenoxide) (2).

$^1$H-NMR (400 MHz, CDCl$_3$): 8.03 (dd, 1H), 7.6 (dd, 1H), 7.25–7.2 (m, 2H), 7.15 (m, 1H), 7.1–7.0 (m, 2H), 6.9 (m, 1H), 6.8 (s, 1H), 6.75 (m, 1H), 6.7 (m, 1H), 6.3 (s, 1H), 5.55 (d, 1H), 2.65 (s, 3H), 2.3 (s, 3H), 1.3 (s, 3H), 1.25 (s, 9H), 1.22 (s, 3H), 1.15 (s, 9H).

Solubility Comparison:

50 mg of dimethylsilanediylbis(2-methylindenyl)zirconium dichloride dissolved completely in 50 ml of toluene at room temperature (solubility about 2.1 mmol/l).

50 mg of compound (2) dissolved immediately in <5 ml of toluene at room temperature (solutility >15 mmol/l).

EXAMPLE 3

Dimethylsilanediylbis(2-methyl-4,5-benzoindenyl)zirconium monochloride mono(2-isopropyl-5-methylphenoxide) (3)

2.7 g (17.4 mmol) of 2-isopropyl-5-methylphenol in 20 ml of toluene/2 ml of THF were admixed at room temperature with 6.5 ml (17.4 mmol) of a 20% strength solution of butyllithium in toluene. The mixture was stirred for another 1 hour at 60° C. At room temperature, 5.0 g (8.7 mmol) of dimethylsilanediylbis(2-methyl-4,5-benzoindenyl)zirconium dichloride were added as a solid. The suspension was stirred for 4 hours at 100° C. and subsequently filtered hot through Celite. The filter cake was extracted twice with 25 ml each time of toluene (100° C.). After evaporation of part of the solvent, the yellow solid which precipitated was filtered off and dried under reduced pressure. This gave 2.5 g (41%) of dimethylsilanediylbis(2-methyl-4,5-benzoindenyl)zirconium monochloride mono(2-isopropyl-5-methylphenoxide) (3).

$^1$H-NMR (400 MHz, CDCl$_3$): 7.9 (dd, 1H), 7.81 (m, 1H), 7.74 (m, 1H), 7.54 (m, 2H), 7.45–7.08 (m, 8H), 6.65 (d, 1H), 6.55 (s, 1H), 6.35 (m, 1H), 5.56 (d, 1H), 2.58 (s, 3H), 2.35 (s, 3H), 2.3 (m, 1H), 2.1 (s, 3H), 1.37 (s, 3H), 1.27 (s, 3H), 0.75 (d, 3H), 0.62 (d, 3H).

Solubility Comparison:

50 mg of dimethylsilanediylbis(2-methyl-4,5-benzoindenyl)zirconium dichloride dissolved completely in 240 ml of toluene at room temperature (solubility about 0.36 mmol/l).

50 mg of compound (3) dissolved in 4 ml of toluene at room temperature (solubility about 18 mmol/l).

EXAMPLE 4

Dimethylsilanediylbis(2-methylindenyl)zirconium monochloride mono(2-isopropyl-5-methylphenoxide) (4)

3.2 g (21 mmol) of 2-isopropyl-5-methylphenol in 20 ml of toluene/2 ml of THF were admixed at room temperature with 7.8 ml (21 mmol) of a 20% strength solution of butyllithium in toluene. The mixture was stirred for another 1 hour at 60° C. At room temperature, 5.0 g (10.5 mmol) of dimethylsilanediylbis(2-methylindenyl)zirconium dichloride were added as a solid. The suspension was stirred for 2 hours at 100° C. and subsequently filtered hot through Celite. The filter cake was extracted twice with 25 ml each time of toluene (100° C.). After evaporation of part of the solvent, the yellow solid which precipitated was filtered off and dried under reduced pressure. This gave 1.36 g (22%) of dimethylsilanediylbis(2-methylindenyl)zirconium monochloride mono(2-isopropyl-5-methylphenoxide) (4).

1H-NMR (400 MHz, CDCl$_3$): 8.0 (m, 1H), 7.81 (m, 1H), 7.3–6.8 (m, 8H), 6.55 (dm, 1H), 6.1 (s, 1H), 5.9 (d, 1H), 2.7 (hept, 1H), 2.45 (s, 3H), 2.25 (s, 3H), 2.18 (s, 3H), 1.4 (s, 3H), 1.25 (s, 3H), 1.1 (d, 3H), 0.95 (d, 3H).

Solubility Comparison:

50 mg of dimethylsilanediylbis(2-methylindenyl)zirconium dichloride dissolved completely in 50 ml of toluene at room temperature (solubility about 2.1 mmol/l).

50 mg of compound (4) dissolved in 5 ml of toluene at room temperature (solubility about 17 mmol/l).

EXAMPLE 5

Dimethylsilanediylbis(2-methylindenyl)zirconium monochloride mono(2,4-di-methylphenoxide) (5)

1.0 g (8.2 mmol) of 2,4-dimethylphenol in 20 ml of toluene/2 ml of THF was admixed at room temperature with 3.0 ml (8.2 mmol) of a 20% strength solution of butyllithium in toluene. The mixture was stirred for another 1 hour at 60° C. At room temperature, 1.9 g (4.0 mmol) of dimethylsilanediylbis(2-methylindenyl)zirconium dichloride were added as a solid. The suspension was stirred for 8 hours at 60° C. and subsequently filtered hot through Celite. After evaporation of the solvent to leave a volume of about 7 ml, the yellow solid which precipitated at −30° C. was filtered off and dried under reduced pressure. This gave 0.65 g (29%) of dimethylsilanediylbis(2-methylindenyl)zirconium monochloride mono(2,4-di-methylphenoxide) (5).

$^1$H-NMR (400 MHz, CDCl$_3$): 7.96 (dd, 1H), 7.6 (m, 1H), 7.36 (m, 1H), 7.31 (m, 1H), 7.29 (d, 1H), 7.1 (m, 1H), 6.99 (m, 1H), 6.94 (m, 1H), 6.88 (s, 1H), 6.75 (m, 1H), 6.65 (m, 1H), 6.06 (s, 1H), 5.93 (d, 1H), 2.4 (s, 3H), 2.24 (s, 3H), 2.18 (s, 3H), 1.85 (s, 3H), 1.35 (s, 3H), 1.24 (s, 3H).

EXAMPLE 6

Dimethylsilanediylbis(2-methyl-4,5-benzoindenyl) zirconium monochloride mono(2,4-di-tert-pentylphenoxide) (6)

0.85 g (3.5 mmol) of 2,4-di-tert-pentylphenol in 10 ml toluene/1 ml of THF was admixed at room temperature with 1.3 ml (3.5 mmol) of a 20% strength solution of butyllithium in toluene. The mixture was stirred for another 1 hour at 60° C. At room temperature, 1.0 [lacuna] (1.74 mmol) of dimethylsilanediylbis(245 methyl-4,5-benzoindenyl)zirconium dichloride was added as a solid. The suspension was stirred for 4 hours at 100° C., diluted with 40 ml of toluene and subsequently filtered hot through Celite. The filter cake was extracted twice with 25 ml each time of toluene (100° C.). After evaporation of the solvent to leave a volume of 10 ml, the yellow solid which precipitated was filtered off, washed with a little cold toluene and dried under reduced pressure. This gave 0.85 g (63%) of dimethylsilanediylbis(2-methyl-4,5-benzoindenyl)zirconium monochloride mono(2,4-di-tert-pentylphenoxide) (6).

$^1$H-NMR (400 MHz, CDCl$_3$): 8.00 (d, 1H), 7.74 (t, 2H), 7.64–7.57 (m, 2H), 7.45–7.27 (m, 5H), 7.14 (s, 1H), 7.10 (m, 1H), 6.98 (m, 1H), 6.78 (s, 1H), 6.65 (d, 1H), 6.52 (dd, 1H), 5.38 (d, 1H), 2.78 (s, 3H), 2.41 (s, 3H), 1.46 (quart., 2H), 1.41 (s, 3H), 1.30 (s, 3H), 1.22 (m, 2H), 1.14 (s, 3H), 1.13 (s, 3H), 0.91 (s, 3H), 0.88 (s, 3H), 0.57 (t, 3H), 0.39 (t, 3H).

Solubility Comparison:

50 mg of dimethylsilanediylbis(2-methyl-4,5-benzoindenyl)zirconium dichloride dissolved completely in 240 ml of toluene at room temperature (solubility about 0.36 mmol/l).

55 mg of compound (6) dissolved in 4 ml of toluene at room temperature (solubility about 17.7 mmol/l).

We claim:

1. A compound of the formula (I),

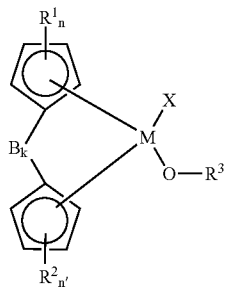

where

M is Ti, Zr or Hf,

R$^1$ are identical or different and are each a radical Si(R$^{12}$)$_3$, where R$^{12}$ are identical or different and are each a hydrogen atom or a C$_1$–C$_{40}$-group, or R$^1$ is a C$_1$–C$_{30}$-group, or two or more radicals R$^1$ may be connected to one another in such a way that the radicals R$^1$ and the atoms of the cyclopentadienyl ring which connect them form a C$_4$–C$_{24}$-ring system which may in turn be substituted, R$^2$ are identical or different and are each a radical Si(R$^{12}$), where R$^{12}$ are identical or different and are each a hydrogen atom or a C$_1$–C$_{40}$-group, or R$^2$ is a C$_1$–C$_{30}$-group, or two or more radicals R$^2$ may be connected to one another in such a way that the radicals R$^2$ and the atoms of the cyclopentadienyl ring which connected them form a C$_4$–C$_{24}$-ring system which may in turn be substituted, R$_3$ is C$_7$–C$_{30}$-alkylaryl, fluorinated C$_6$–C$_{24}$-aryl, or fluorinated C$_7$–C$_{30}$-alkylaryl, X is a halogen atom, n is from 0 to 4, n' is from to 4, k is 1, B is a bridging structural element between the two cyclopentadienyl rings defined as M$^3$R$^{13}$R$^{14}$, wherein M$^3$ is carbon or silicon and R$^{13}$ and R$^{14}$ are identical or different and are C$_1$–C$_{10}$-alkyl, C$_6$–C$_{14}$-aryl or trimethyl silyl, and one or both cyclopentadienyl rings are substituted in such a way that they form an indenyl ring.

2. The compound of claim 1 having the formula

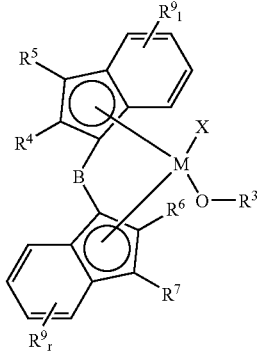

where

R$^4$–R$^7$ are identical or different and are each a hydrogen atom or a C$_1$–C$_{20}$-group, R$^8$, R$^9$ are identical or different and are each a hydrogen atom, a halogen atom or a C$_1$–C$_{20}$-group, and two radicals R$^8$ or R$^9$ may form a monocylic or polycyclic ring system which may in turn be substituted, R$^3$, M, X and B are as previously defined, and l, l' are identical or different and are each an integer from zero to 4.

3. The compound of claim 2 wherein X is chlorine.

4. The compound of claim 2 wherein the indenyl ings are identical.

5. The compound of claim 4 wherein M is Zr, the indenyl rings are 2-methyl-4,5-benzoindenyl or 2-methyl-indenyl and X is chlorine.

6. The compound of claim 5 wherein the indenyl rings are 2-methyl-4,5-benzoindenyl.

7. The compound of claim 6 wherein R$^3$ is 2,4-di-tert-butyl-phenyl, 2,4-di-tert-pentyl-phenyl or 2-isopropyl-5-methyl-phenyl.

8. The compound of claim 7 wherein B is dimethylsilanediyl.

9. The compound of claim 5 wherein the indenyl rings are 2-methyl-indenyl.

10. The compound of claim 9 wherein $R^3$ is 2,4-di-tert-butyl-phenyl or 2-isopropyl-5-methyl-phenyl.

11. The compound of claim 10 wherein B is dimethylsilanediyl.

12. The compound of claim 4 wherein B is $SiR^{13}R^{14}$ where $R^{13}$ and $R^{14}$ are identical or different and are each Me or Ph.

13. The compound of claim 1, wherein the moiety $MX(OR^3)$ is zirconium monochloride mono(2,4-di-tert-butylphenoxide),
zirconium monochloride mono(2,6-di-tert-butylphenoxide),
zirconium monochloride mono(3,5-di-tert-butylphenoxide),
zirconium monochloride mono(2,6-di-sec-butylphenoxide),
zirconium monochloride mono(2,4-di-methylphenoxide),
zirconium monochloride mono(2,3-di-methylphenoxide),
zirconium monochloride mono(2,5-di-methylphenoxide),
zirconium monochloride mono(2,6-di-methylphenoxide),
zirconium monochloride mono(3,4-di-methylphenoxide),
zirconium monochloride mono(3,5-di-methylphenoxide),
zirconium monochloride mono(2-methylphenoxide),
zirconium monochloride mono(3-methylphenoxide),
zirconium monochloride mono(4-methylphenoxide),
zirconium monochloride mono(2-ethylphenoxide),
zirconium monochloride mono(3-ethylphenoxide),
zirconium monochloride mono(4-ethylphenoxide),
zirconium monochloride mono(2-sec-butylphenoxide),
zirconium monochloride mono(2-tert-butylphenoxide),
zirconium monochloride mono(3-tert-butylphenoxide),
zirconium monochloride mono(4-sec-butylphenoxide),
Zirconium monochloride mono(4-tert-butylphenoxide),
zirconium monochloride mono(2-isopropyl-5-methylphenoxide),
zirconium monochloride mono(4-isopropyl-3-methylphenoxide),
zirconium monochloride mono(5-isopropyl-2-methylphenoxide),
zirconium monochloride mono(5-isopropyl-3-methylphenoxide),
zirconium monochloride mono(2,4-bis (2-methyl-2-butyl)phenoxide),
zirconium monochloride mono(2,6-di-tert-butyl-4-methylphenoxide),
zirconium monochloride mono(4-nonylphenoxide),
zirconium monochloride mono(isopropylphenoxide),
zirconium monochloride mono(propylphenoxide),
zirconium monochloride mono(trimethylphenoxide),
zirconium monochloride mono(tert-butyl-methylphenoxide),
zirconium monochloride mono(2-tert-butyl-methylphenoxide),
zirconium monochloride mono(2,6-diisopropylphenoxide),
zirconium monochloride mono(4-octylphenoxide) or
zirconium monochloride mono(2,6-di-tert-butyl-4-ethylphenoxide).

14. The compound of claim 2 wherein the moiety $MX(OR^3)$ is zirconium monochloride mono(2,4-di-tert-butylphenoxide),
zirconium monochloride mono(2,6-di-tert-butylphenoxide),
zirconium monochloride mono(3,5-di-tert-butylphenoxide),
zirconium monochloride mono(2,6-di-sec-butylphenoxide),
zirconium monochloride mono(2,4-di-methylphenoxide),
zirconium monochloride mono(2,3-di-methylphenoxide),
zirconium monochloride mono(2,5-methylphenoxide),
zirconium monochloride mono(2,6-di-methylphenoxide),
zirconium monochloride mono(3,4-di-methylphenoxide),
zirconium monochloride mono(3,5-di-methylphenoxide),
zirconium monochloride mono(2-methylphenoxide),
zirconium monochloride mono(3-methylphenoxide),
zirconium monochloride mono(4-methylphenoxide),
zirconium monochloride mono(2-ethylphenoxide),
zirconium monochloride mono(3-ethylphenoxide),
zirconium monochloride mono(4-ethylphenoxide),
zirconium monochloride mono(2-sec-butylphenoxide),
zirconium monochloride mono(2-t-butylphenoxide),
zirconium monochloride mono(3-tert-butylphenoxide),
zirconium monochloride mono(4-sec-butylphenoxide),
zirconium monochloride mono(4-tert-butylphenoxide),
zirconium monochloride mono(2-isopropyl-5-methylphenoxide),
zirconium monochloride mono(4-isopropyl-3-methylphenoxide),
zirconium monochloride mono(5-isopropyl-2-methylphenoxide),
zirconium monochloride mono(5-isopropyl-3-methylphenoxide),
zirconium monochloride mono(2,4-bis (2-methyl-2-butyl)phenoxide),
zirconium monochloride mono(2,6-di-tert-butyl-4-methylphenoxide),
zirconium monochloride mono(4-nonylphenoxide),
zirconium monochloride mono(isopropylphenoxide),
zirconium monochloride mono(propylphenoxide),
zirconium monochloride mono(trimethylphenoxide),
zirconium monochloride mono(tert-butyl-methylphenoxide),
zirconium monochloride mono(2-tert-butyl-4-ethylphenoxide),
zirconium monochloride mono(2,6-diisopropylphenoxide),
zirconium monochloride mono(4-octylphenoxide) or
zirconium monochloride mono(2,6-di-tert-butyl-4-ethylphenoxide).

15. The compound of claim 1 wherein the solubility of said compound of formula (I) measured as molar concentration in toluene at room temperature is at least doubled compared with the solubility of the corresponding metallocene dichloride wherein X is Cl and $OR^3$ is Cl.

16. The compound of claim 2 wherein the solubility of said compound of formula (I) measured as molar concentration in toluene at room temperature is at least doubled compared with the solubility of the corresponding metallocene dichloride wherein X is Cl and $OR^3$ is Cl.

17. A catalyst comprising at least one compound as claimed in claim 1, a support and a cocatalyst.

18. A process for preparing a polyolefin which comprises polymerizing an olefinic monomer in the presence of a catalyst as claimed in claim 17.

* * * * *

UNITED STATES PATENT AND TRADEMARK OFFICE
CERTIFICATE OF CORRECTION

| | | |
|---|---|---|
| PATENT NO. | : 7,053,160 B1 | Page 1 of 1 |
| APPLICATION NO. | : 09/701658 | |
| DATED | : May 30, 2006 | |
| INVENTOR(S) | : Bingel et al. | |

It is certified that error appears in the above-identified patent and that said Letters Patent is hereby corrected as shown below:

In The Claims

Col. 28, indicated lines 25 – 30: "$R^9_1$" in the formula should read --$R^8_1$--

Col. 29, indicated line 34: "Zirconium" should be replaced by --zirconium--

Col. 29, indicated lines 53 and 54: "mono(2-tert-butyl-methylphenoxide)" should be replaced by --mono(2-tert-butyl-4-methylphenoxide)--

Col. 30, indicated line 19: "mono(2-t-butylphenoxide)" should be replaced by --mono(2-tert-butylphenoxide)--

Signed and Sealed this

Tenth Day of April, 2007

JON W. DUDAS
*Director of the United States Patent and Trademark Office*